(12) United States Patent
Diab et al.

(10) Patent No.: US 6,206,830 B1
(45) Date of Patent: *Mar. 27, 2001

(54) SIGNAL PROCESSING APPARATUS AND METHOD

(75) Inventors: Mohamed Kheir Diab; Esmaiel Kiani-Azarbayjany, both of Laguna Niguel, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/441,736

(22) Filed: Nov. 17, 1999

Related U.S. Application Data

(63) Continuation of application No. 09/102,131, filed on Jun. 22, 1998, now Pat. No. 6,036,642, which is a continuation of application No. 08/479,918, filed on Jun. 7, 1995, now Pat. No. 5,769,785, which is a continuation of application No. 08/249,690, filed on May 26, 1994, now Pat. No. 5,482,036, which is a continuation of application No. 07/666,000, filed on Mar. 7, 1991, now abandoned.

(51) Int. Cl.$^7$ ........................................................ A61B 5/02
(52) U.S. Cl. ............................................................. 600/364
(58) Field of Search ........................... 600/485, 500–503, 600/561, 300, 324, 364–365, 473, 476–479; 356/39–41; 379/410–411

(56) References Cited

U.S. PATENT DOCUMENTS

| 3,647,299 | 3/1972 | Lavallee . |
| 3,704,706 | 12/1972 | Herczfeld et al. . |
| 4,063,551 | 12/1977 | Sweeney . |

(List continued on next page.)

FOREIGN PATENT DOCUMENTS

| 341 327 | 11/1989 | (EP) . |
| 2166326 | 4/1986 | (GB) . |
| 2235288 | 2/1991 | (GB) . |

OTHER PUBLICATIONS

Neuman, Michael R., "Pulse Oximetry: Physical Principles, Technical Realization and Present Limitations", *Continuous Transcutaneous Monitoring*, Plenum Press, New York, 1987, pp. 135–144.

(List continued on next page.)

*Primary Examiner*—Cary O'Connor
*Assistant Examiner*—Ryan Carter
(74) *Attorney, Agent, or Firm*—Knobbe, Martens, Olson & Bear, LLP

(57) ABSTRACT

A signal processor which acquires a first signal, including a first desired signal portion and a first undesired signal portion, and a second signal, including a second desired signal portion and a second undesired signal portion, wherein the first and second desired signal portions are correlated. The signals may be acquired by propagating energy through a sodium and measuring an attenuated signal after transmission or reflection. Alternatively, the signals may be acquired by measuring energy generated by the medium. A processor of the present invention generates a noise reference signal which is a combination of only the undesired signal portions and is correlated to both the first and second undesired signal portions. The noise reference signal is then used to remove the undesired portion of each of the first and second measured signals via an adaptive noise canceler, preferably of the joint process estimator type. The processor of the present invention may be employed in conjunction with an adaptive noise canceler in physiological monitors wherein the known properties of energy attenuation through a medium are used to determine physiological characteristics of the medium. Many physiological conditions, such as the pulse of a patient or the concentration of a constituent in a medium, can be determined from the desired portion of the signal after undesired signal portions, such as those caused by erratic notion, are removed.

30 Claims, 11 Drawing Sheets .

U.S. PATENT DOCUMENTS

| | | |
|---|---|---|
| 4,086,915 | 5/1978 | Kofsky et al. . |
| 4,095,117 | 6/1978 | Nagy . |
| 4,407,290 | 10/1983 | Wilber . |
| 4,537,200 | 8/1985 | Widrow . |
| 4,649,505 | 3/1987 | Zinser, Jr. et al. . |
| 4,773,422 | 9/1988 | Issacson et al. . |
| 4,799,493 | 1/1989 | DuFault . |
| 4,800,495 | 1/1989 | Smith . |
| 4,824,242 | 4/1989 | Frick et al. . |
| 4,848,901 | 7/1989 | Hood, Jr. . |
| 4,860,759 | 8/1989 | Kahn et al. . |
| 4,863,265 | 9/1989 | Flower et al. . |
| 4,867,571 | 9/1989 | Frick et al. . |
| 4,869,253 | 9/1989 | Craig, Jr. et al. . |
| 4,869,254 | 9/1989 | Stone et al. . |
| 4,883,353 | 11/1989 | Hausman . |
| 4,892,101 | 1/1990 | Cheung et al. . |
| 4,907,594 | 3/1990 | Muz . |
| 4,911,167 | 3/1990 | Corenman et al. . |
| 4,927,264 | 5/1990 | Shiga et al. . |
| 4,928,692 | 5/1990 | Goodman et al. . |
| 4,948,248 | 8/1990 | Lehman . |
| 4,955,379 | 9/1990 | Hall . |
| 4,956,867 | 9/1990 | Zurek et al. . |
| 4,960,126 | 10/1990 | Conlon et al. . |
| 5,057,695 | 10/1991 | Hirao et al. . |
| 5,273,036 | 12/1993 | Kronberg et al. . |
| 5,431,170 | 7/1995 | Mathews . |
| 5,490,505 | 2/1996 | Diab . |
| 5,769,785 * | 6/1998 | Diab et al. ............................ 600/364 |

OTHER PUBLICATIONS

Mook, G.A., et al., "Wavelength dependency of the spectrophotometric determination of blood oxygen saturation", *Clinical Chemistry Acta*, vol. 26, pp. 170–173, 1969.

Klimasauskas, Casey, "Neural Nets and Noise Filtering", *Dr. Dobb's Journal*, Jan. 1989, p. 32.

Melnikof, S. "Neural Networks for Signal Processing: A Case Study", *Dr. Dobbs Journal*, Jan. 1989, pp. 36–37.

Widrow, Bernard, *Adaptive Signal Processing*, Prentice Hall, Englewood, NJ, 1985

Cohen, Arnon, "Volume I: Time and Frequency Domains Analysis", *Biomedical Signal Processing*, CRC Press, Inc., Boca Raton, FL, pp. 152–159.

Severinghaus, J.W., "Pulse Oximetry Uses and Limitations", pp. 104, ASA Convention, New Orleans, 1989.

Mook, G.A., et al., "Spectrophotometric Determination of Oxygen Saturation of Blood Independent of the Presence of Indocyanine Green", *Cardiovascular Research*, vol. 13, pp. 233–237, 1979.

Harris et al, *Digital Signal Processing with Efficient Polyphase Recursive All–Pass Filters*, International Conference, Italy, 9/4–6, 1991.

Rabiner, Lawrence et al., *Theory and Application of Digital signal Processing*, 1975, p. 260.

Tremper, Kevin K. et al, "Pulse Oximetry: Technical Aspects of Machine Design", Advances in Oxygen Monitoring, pp. 137–153, 1987.

Brown, D.P., "Evaluation of Pulse Oximeters Using Theoretical Models and Experimental Studies", Master Thesis, University of Washington, Nov. 25, 1987.

Haykin, S, *Adaptive Filter Theory*, Prentice Hall, Englewood Cliffs, NJ 1991.

* cited by examiner

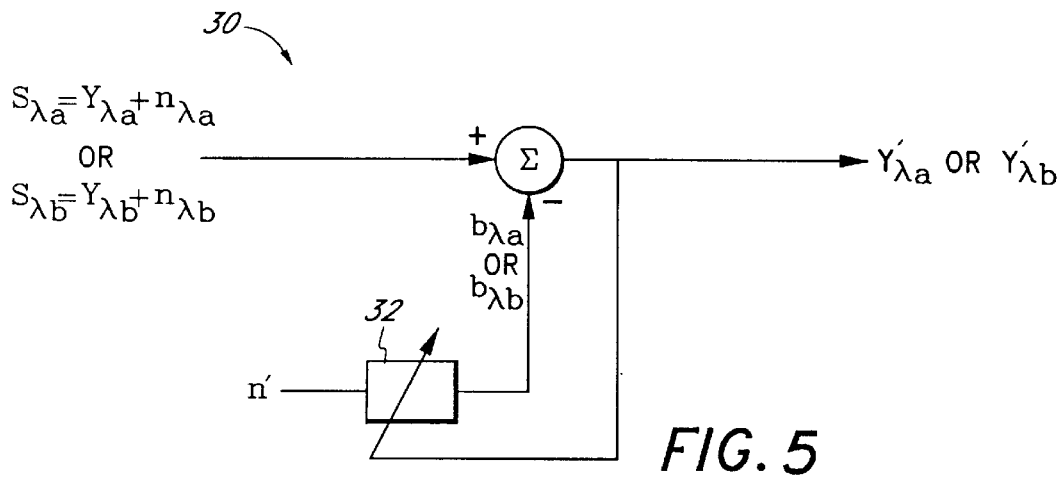
FIG. 5
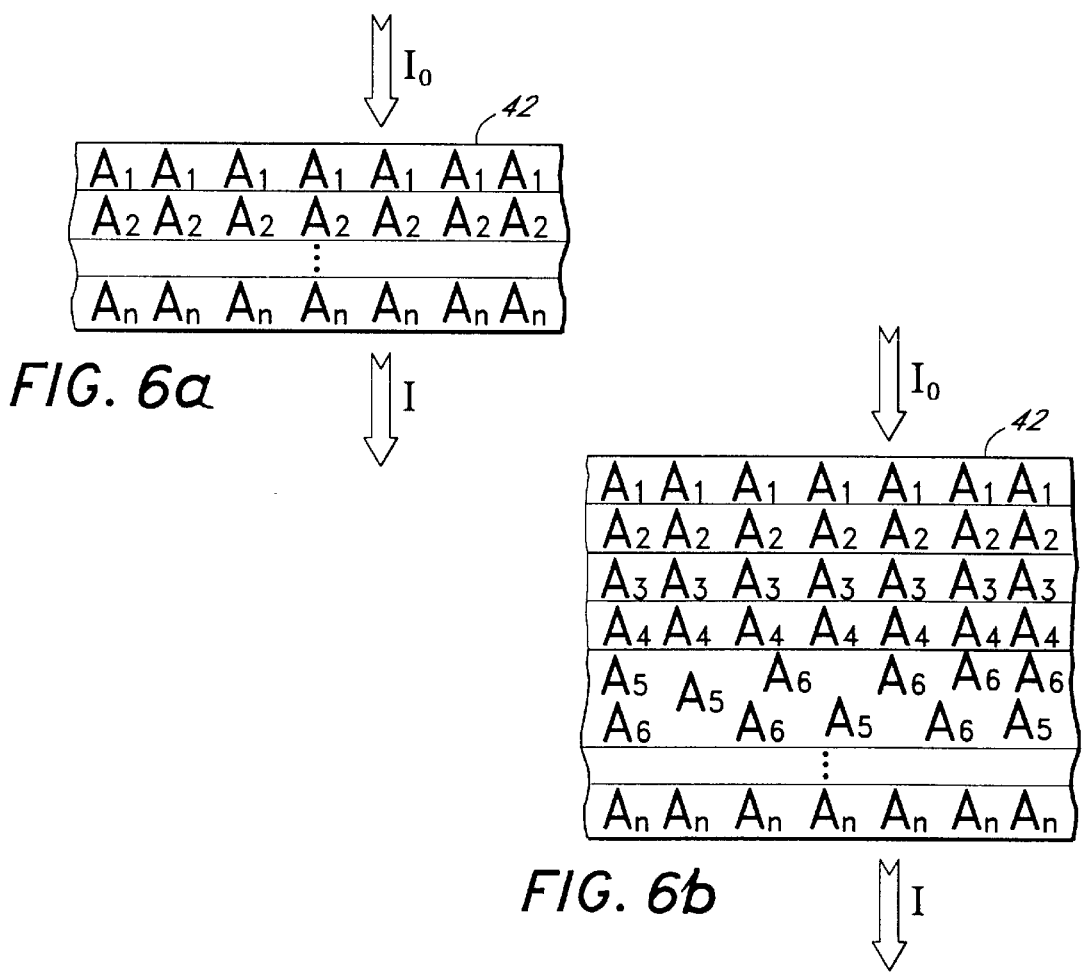
FIG. 6a
FIG. 6b

SIGNAL PROCESSING APPARATUS AND METHOD

The present application is a continuation of application Ser. No. 09/102,131, now U.S. Pat. No. 6,036,642, filed Jun. 22, 1998, which is a continuation of application Ser. No. 08/479,918, now U.S. Pat. No. 5,769,785, filed Jun. 7, 1995, which is a continuation of application Ser. No. 08/249,690, now U.S. Pat. No. 5,482,036, filed May 26, 1994, which is a continuation of application Ser. No. 07/666,060 filed Mar. 7, 1991, now abandoned.

FIELD OF THE INVENTION

The present invention relates to the field of signal processing. More specifically, the present invention relates to the processing of measured signals to remove undesired portions when little is known about the undesired signal portion.

BACKGROUND OF THE INVENTION

Signal processors are typically employed to remove undesired portions from a composite measured signal including a desired signal portion and an undesired signal portion. If the undesired signal portion occupies a different frequency spectrum than the desired signal. .then conventional filtering techniques such as low pass, band pass, and high pass filtering could be used to separate the desired portion from the total signal. Fixed single or multiple notch filters could also be employed if the undesired signal portions(s) exist at a fixed frequency(s).

However, it is often the case that an overlap in frequency spectrum between the desired and undesired signal portions does exist and the statistical properties of both signal portions change with time. In such cases, conventional filtering techniques are totally ineffective in extracting the desired signal. If, however, a description of the undesired portion can be made available, adaptive noise canceling can be employed to remove the undesired portion of the signal leaving the desired portion available for measurement. Adaptive noise cancelers dynamically change their transfer function to adapt to and remove the undesired signal portions of a composite signal. Adaptive noise cancelers require a noise reference signal which is correlated to the undesired signal portion. The noise reference signal is not necessarily a representation of the undesired signal portion, but has a frequency spectrum which is similar to that of the undesired signal. In many cases, it requires considerable ingenuity to determine a noise reference signal since nothing is a priori known about the undesired signal portion.

One area where composite measured signals comprise a desired signal portion and an undesired signal portion about which no information can easily be determined is physiological monitoring. Physiological—monitoring apparatuses generally measure signals derived from a physiological system, such as the human body. Measurements which are typically taken with physiological monitoring systems include electron cardiographs, blood pressure, blood gas saturation (such as oxygen saturation), capnographs, heart rate, respiration rate, and depth of anesthesia, for example. Other types of measurements include those which measure the pressure and quantity of a substance within the body such as breathalizer testing, drug testing, cholesterol testing, glucose testing, arterial carbon dioxide testing, protein testing, and carbon monoxide testing, for example. The source of the undesired signal portion in these measurements is often due to motion of the patient, both external and internal (muscle movement, for example), during the measurement process.

Knowledge of physiological systems, such as the amount of oxygen in a patient's blood, can be critical, for example during surgery. Data can be determined by a lengthy invasive procedure of extracting and testing matter, such as blood, from a patient, or by more expedient, non-invasive measures. Many types of non-invasive measurements can be made by using the known properties of energy attenuation as a selected form of energy passes through a medium.

Energy is caused to be incident on a medium either derived from or contained within a patient and the amplitude of transmitted or reflected energy is then measured. The amount of attenuation of the incident energy caused by the medium is strongly dependent on the thickness and composition of the medium through which the energy must pass as well as the specific form of energy selected. Information about a physiological system can be derived from data taken from the attenuated signal of the incident energy transmitted through the medium if the noise can be removed. However, non-invasive measurements often do not afford the opportunity to selectively observe the interference causing the undesired signal portion, making it difficult to remove.

These undesired signal portions often originate from both AC and DC sources. The first undesired portion is an easily removed DC component caused by transmission of the energy through differing media which are of relatively constant thickness within the body, such as bone, tissue, skin, blood, etc. Second, is an erratic AC component caused when differing media being measured are perturbed and thus, change in thickness while the measurement is being made. Since most materials in and derived from the body are easily compressed, the thickness of such matter changes if the patient moves during a non-invasive physiological measurement. Patient movement can cause the properties of energy attenuation to vary erratically. Traditional signal filtering techniques are frequently totally ineffective and grossly deficient in removing these motion induced effects from a signal. The erratic or unpredictable nature of motion induced undesired signal components is the major obstacle in removing them. Thus, presently available physiological monitors generally become totally inoperative during time periods when the patient moves.

A blood gas monitor is one example of a physiological monitoring system which is based upon the measurement of energy attenuated by biological tissues or substances. Blood gas monitors transmit light into the tissue and measure the attenuation of the light as a function of time. The output signal of a blood gas monitor which is sensitive to the arterial blood flow contains a component which is a waveform representative of the patient's arterial pulse. This type of signal, which contains a component related to the patient's pulse, is called a plethysmographic wave, and is shown in FIG. 1 as curve Y. Plethysmographic waveforms are used in blood pressure or blood gas saturation measurements, for example. As the heart beats the amount of blood in the arteries increases and decreases, causing increases and decreases in energy attenuation, illustrated by the cyclic wave Y in FIG. 1.

Typically, a digit such as a finger, an ear lobe, or other portion of the body where blood flows close to the skin, is employed as the medium through which light energy is transmitted for blood gas attenuation measurements. The finger comprises skin, fat, bone, muscle, etc., shown schematically in FIG. 2, each of which attenuates energy incident on the finger in a generally predictable and constant manner.

However, when fleshy portions of the finger are compressed erratically, for example by motion of the finger, energy attenuation becomes erratic.

An example of a more realistic measured waveform S is shown in FIG. 3, illustrating the effect of motion. The desired portion of the signal Y is the waveform representative of the pulse, corresponding to the sawtooth-like pattern wave in FIG. 1. The large, motion-induced excursions in signal amplitude hide the desired signal Y. It is easy to see how even small variations in amplitude make it difficult to distinguish the desired signal Y in the presence of a noise component n.

A specific example of a blood gas monitoring apparatus is a pulse oximeter which measures the saturation of oxygen in the blood. The pumping of the heart forces freshly oxygenated blood into the arteries causing greater energy attenuation. The saturation of oxygenated blood may be determined from the depth of the valleys relative to the peaks of two plethysmographic waveforms measured at separate wavelengths. However, motion induced undesired signal portions, or motion artifacts, must be removed from the measured signal for the oximeter to continue the measurement during periods when the patient moves.

SUMMARY OF THE INVENTION

The present invention is a signal processor which acquires a first signal and a second signal that is correlated to the first signal. The first signal comprises first desired signal portion and a first undesired signal portion. The second signal comprises a second desired signal portion and a second undesired signal portion. The signals may be acquired by propagating energy through a medium and measuring an attenuated signal after transmission or reflection. Alternatively, the signal may be acquired by measuring energy generated by the medium.

The first and second measured signals are processed to generate a noise reference signal which does not contain the desired signal portions from either of the first or second measured signals. The remaining undesired signal portions from the first and second measured signals are combined to form a noise reference signal. This noise reference signal is correlated to the undesired signal portion of each of the first and second measured signals.

The noise reference signal is then used to remove the undesired portion of each of the first and second measured signals via an adaptive noise canceler. An adaptive noise canceler can be described by analogy to a dynamic multiple notch filter which dynamically changes its transfer function in response to the noise reference signal and the measured signals to remove frequencies from the measured signals that are also present in the noise reference signal. Thus, a typical adaptive noise canceler receives the signal from which it is desired to remove noise and a noise reference signal. The output of the adaptive noise canceler is a good approximation to the desired signal with the noise removed.

Physiological monitors can often advantageously employ signal processors of the present invention. Often in physiological measurements a first signal comprising a first desired portion and a first undesired portion and a second signal comprising a second desired portion and a second undesired portion are acquired. The signals may be acquired by propagating energy through a patient's body (or a material which is derived from the body, such as breath, blood, or tissue, for example) and measuring an attenuated signal after transmission or reflection. Alternatively, the signal may be acquired by measuring energy generated by a patient's body, such as in electrocardiography. The signals are processed via the signal processor of the present invention to acquire a noise reference signal which is input to an adaptive noise canceler.

One physiological monitoring apparatus which can advantageously incorporate the features of the present invention is a monitoring system which determines a signal which is representative of the arterial pulse, called a plethysmographic wave. This signal can be used in blood pressure calculations, blood gas saturation measurements, etc. A specific example of such a use is in pulse oximetry which determines the saturation of oxygen in the blood. In this configuration, the desired portion of the signal is the arterial blood contribution to attenuation of energy as it passes through a portion of the body where blood flows close to the skin. The pumping of the heart causes blood flow to increase and decrease in the arteries in a periodic fashion, causing periodic attenuation wherein the periodic waveform is the plethysmographic waveform representative of the pulse.

A physiological monitor particularly adapted to pulse oximetry oxygen saturation measurement comprises two light emitting diodes (LED's) which emit light at different wavelengths to produce first and second signals. A detector registers the attenuation of the two different energy signals after each passes through an absorptive media, for example a digit such as a finger, or an earlobe. The attenuated signals generally comprise both desired and undesired signal portions. A static filtering system, such as a band pass filter, removes a portion of the undesired signal which is static, or constant, or outside of a known bandwidth of interest, leaving an erratic or random undesired signal portion, often caused by motion and often difficult to remove, along with the desired signal portion.

Next, a processor of the present invention removes the desired signal portions from the measured signals yielding a noise reference signal which is a combination of the remaining undesired signal portions. The noise reference signal is correlated to both of the undesired signal portions. The noise reference signal and at least one of the measured signals are input to an adaptive noise canceler which removes the random or erratic portion of the undesired signal. This yields a good approximation to the desired plethysmographic signal as measured at one of the measured signal wavelengths. As is known in the art, quantitative measurements of the amount of oxygenated blood in the body can be determined from the plethysmographic signal in a variety of ways.

One aspect of the present invention is a signal processor comprising a detector for receiving a first signal which travels along a first propagation path and a second signal which travels along a second propagation path wherein a portion of the first and second propagation paths are located in a propagation medium. The first signal has a -first desired signal portion and a first undesired signal portion and the second signal has a second desired signal portion and a second undesired signal portion. The first and second undesired signal portions are a result of a perturbation of the propagation medium. This aspect of the invention additionally comprises a reference processor having an input for receiving the first and second signals. The processor is adapted to combine the first and second signals to generate a reference signal having a primary component which is a function of the first and said second undesired signal portions.

The above described aspect of the present invention may further comprise an adaptive signal processor for receiving the reference signal and the first signal and for deriving therefrom an output signal having a primary component which is a function of the first desired signal portion of the first signal. Alternatively, the above described aspect of the present invention my further comprise an adaptive signal processor for receiving the reference signal and the second signal and for deriving therefrom an output signal having a primary component which is a function of the second desired signal portion of the second signal. The adaptive signal processor may comprise an adaptive noise canceler. The adaptive noise canceler may be comprise a joint process estimator having a least-squares-lattice predictor and a regression filter.

The detector in the aspect of the signal processor of the present invention described above may further comprise a sensor for sensing a physiological function. The sensor may comprise a light sensitive device. Additionally, the present invention may further comprising a pulse oximeter for measuring oxygen saturation in a living organism.

Another aspect of the present invention is a physiological monitoring apparatus comprising a detector for receiving a first physiological measurement signal which travels along a first propagation path and a second physiological measurement signal which travels along a second propagation path. A portion of the first and second propagation paths is located in a propagation medium. The first signal has a first desired signal portion and a first undesired signal portion and the second signal has a second desired signal portion and a second undesired signal portion. The physiological monitoring apparatus further comprises a reference processor having an input for receiving the first and second signals. The processor is adapted to combine the first and second signals to generate a reference signal having a primary component which is a function of the first and the second undesired signal portions.

The physiological monitoring apparatus may further comprise an adaptive signal processor for receiving the reference signal and the first signal and for deriving therefrom an output signal having a primary component which is a function of the first desired signal portion of the first signal. Alternatively, the physiological monitoring apparatus may further comprise an adaptive signal processor for receiving the reference signal and the second signal and for deriving therefrom an output signal having a primary component which is a function of the second desired signal portion of the second signal. The physiological monitoring apparatus may further comprise a pulse oximeter.

A further aspect of the present invention is an apparatus for measuring a blood constituent comprising a energy source for directing a plurality of predetermined wavelengths of electromagnetic energy upon a specimen and a detector for receiving the plurality of predetermined wavelengths of electromagnetic energy from the specimen. The detector produces electrical signals corresponding to the predetermined wavelengths in response to the electromagnetic energy. At least two of the electrical signals each has a desired signal portion and an undesired signal portion. Additionally, the apparatus comprises a reference processor having an input for receiving the electrical signals. The processor is configured to combine said electrical signals to generate a reference signal having a primary component which is derived from the undesired signal portions.

This aspect of the present invention may further comprise an adaptive signal processor for receiving the reference signal and one of the two electrical signals and for deriving therefrom an output signal having a primary component which is a function of the desired signal portion of the electrical signal. This may be accomplished by use of an adaptive noise canceler in the adaptive signal processor which may employ a joint process estimator having a least-squares-lattice predictor and a regression filter.

Yet another aspect of the present invention is a blood gas monitor for non-invasively measuring a blood constituent in a body comprising a light source for directing at least two predetermined wavelengths of light upon a body and a detector for receiving the light from the body. The detector, in response to the light from the body, produces at least two electrical signals corresponding to the at least two predetermined wavelengths of light. The at least two electrical signals each has a desired signal portion and an undesired signal portion. The blood oximeter further comprises a reference processor having an input for receiving the at least two electrical signals. The processor is adapted to combine the at least two electrical signals to generate a reference signal with a primary component which is derived from the undesired signal portions. The blood oximeter may further comprise an adaptive signal processor for receiving the reference signal and the two electrical signals and for deriving therefrom at least two output signals which are substantially equal, respectively, to the desired signal portions of the electrical signals.

The present invention also includes a method of determining a noise reference signal from a first signal comprising a first desired signal portion and a first noise portion and a second signal comprising a second desired signal portion and a second noise portion. The method comprises the steps of selecting a signal coefficient which is proportional to a ratio of predetermined attributes of the first desired signal portion and predetermined attributes of the second desired signal portion. The first signal and the second signal coefficient are input into a signal multiplier wherein the first signal is multiplied by the signal coefficient thereby generating a first intermediate signal. The second signal and the first intermediate signal are input into a signal subtractor wherein the first intermediate signal is subtracted from the second signal. This generates a noise reference signal having a primary component which in derived from the first and second noise signal portions. The first and second signals in this method may be derived from light energy transmitted through an absorbing medium.

The present invention further embodies a physiological monitoring apparatus comprising means for acquiring a first signal comprising a first desired signal portion and a first undesired signal portion and a second signal comprising a second desired signal portion and a second undesired signal portion. The physiological monitoring apparatus of the present invention also comprises means for determining from the first and second signals a noise reference signal. Additionally, the monitoring apparatus comprises an adaptive noise canceler having a noise reference input for receiving the noise reference signal and a signal input for receiving the first signal wherein the adaptive noise canceler, in real or near real time, generates an output signal which approximates the first desired signal portion. The adaptive noise canceler may further comprise a joint process estimator.

A further aspect of the present invention is an apparatus for processing an amplitude modulated signal having a signal amplitude complicating feature, the apparatus comprising an energy source for directing electromagnetic energy upon a specimen. Additionally, the apparatus comprises a detector for acquiring a first amplitude modulated signal and a second amplitude modulated signal. Each of the first and second signals has a component containing information about the attenuation of electromagnetic energy by the specimen and a signal amplitude complicating feature. The apparatus includes a reference processor for receiving the first and second amplitude modulated signals and deriving therefrom a noise reference signal which is correlated with the signal amplitude complicating feature. Further, the apparatus incorporates an adaptive noise canceler having a signal input for receiving the first amplitude modulated signal, a noise reference input for receiving the noise reference signal, wherein the adaptive noise canceler produces an output signal having a primary component which is derived from the component containing information about the attenuation off electromagnetic energy by the specimen.

Still another aspect of the present invention is an apparatus for extracting a plethysmographic waveform from an amplitude modulated signal having a signal amplitude complicating feature, the apparatus comprising a light source for transmitting light into an organism and a detector for monitoring light from the organism. The detector produces a first light attenuation signal and a second light attenuation signal, wherein each of the first and second light attenuation signals has a component which is representative of a plethysmographic waveform and a component which is representative of the signal amplitude complicating feature. The apparatus also includes a reference processor for receiving the first and second light attenuation signals and deriving therefrom a noise reference signal. The noise reference signal and the signal amplitude complicating feature each has a frequency spectrum. The frequency spectrum of the noise reference signal is correlated with the frequency spectrum of the signal amplitude complicating feature. Additionally incorporated into this embodiment of the present invention is an adaptive noise canceler having a signal input for receiving the first attenuation signal and a noise reference input for receiving the noise reference signal. The adaptive noise canceler produces an output signal having a primary component which is derived from the component which is representative of a plethysmographic waveform.

The present invention also comprises a method of removing a motion artifact signal from a signal derived from a physiological measurement wherein a first signal having a physiological measurement component and a motion artifact component and a second signal having a physiological measurement component and a motion artifact component are acquired. From the first and second signals a motion artifact noise reference signal which is a primary function of the first and second signals motion artifact components is derived. This method of removing a motion artifact signal from a signal derived from a physiological measurement may also comprise the step of inputting the motion artifact noise reference signal into an adaptive noise canceler to produce an output signal which is a primary function of the first signal physiological measurement component.

BRIEF DESCRIPTION OF THE DRAWINGS

FIG. 5 illustrates an example of an adaptive noise canceler which could be employed in a physiological monitor which also incorporates the processor of the present invention.

FIG. 6a illustrates a schematic absorbing material comprising N constituents within an absorbing material.

FIG. 6b illustrates another schematic absorbing material comprising N constituents within an absorbing material.

DETAILED DESCRIPTION OF THE INVENTION

The present invention is a processor which determines a noise reference signal n'(t) for use in an adaptive noise canceler. An adaptive noise canceler estimates a good approximation Y'(t) to a desired signal Y(t) from a composite signal S(t)=Y(t)+n(t) which, in addition to the desired portion Y(t) comprises an undesired portion n(t). The undesired portion n(t) may contain one or more of a constant portion, a predictable portion, an erratic portion, a random portion, etc. The approximation to the desired signal Y'(t) is derived by removing as many of the undesired portions n(t) from the composite signal S(t) as possible. The constant portion and predictable portion are easily removed with traditional filtering techniques, such as simple subtraction, low pass, band pass, and high pass filtering. The erratic portion is more difficult to remove due to its unpredictable nature. If something is known about the erratic signal, even statistically, it could be removed from the measured signal via traditional filtering techniques. However, it is often the case that no information is known about the erratic portion of the noise. In this case, traditional filtering techniques are usually insufficient. Often no information about the erratic portion of the measured signal is known. Thus, an adaptive noise canceler is utilized in the present invention to remove the erratic portion.

Generally, an adaptive noise canceler has two signal inputs and one output. One of the inputs is the noise reference signal n'(t) which is correlated to the erratic undesired signal portions n(t) present in the composite signal S(t). The other input is for the composite signal S(t). Ideally, the output of the adaptive noise canceler Y'(t) corresponds to the desired signal portion Y(t) only. Often, the most difficult task in the application of adaptive noise cancelers is determining the noise reference signal n'(t) which is correlated to the erratic undesired portion n(t) of the measured signal S(t) since, as discussed above, unpredictable signal portions are usually quite difficult to isolate from the measured signal S(t). In the signal processor of the present invention, a noise reference signal n'(t) is determined from two composite signals measured simultaneously, or nearly simultaneously, at two different wavelengths, $\lambda a$ and $\lambda b$. The signal processor of the present invention can be advantageously used in a monitoring device, such a monitor being well suited for physiological monitoring.

Figure 1:
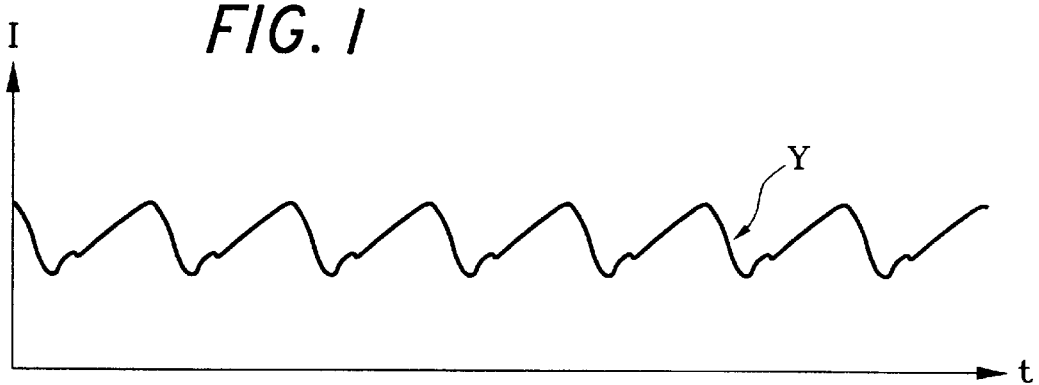
FIG. 1 illustrates an ideal plethysmographic waveform.
Figure 2:
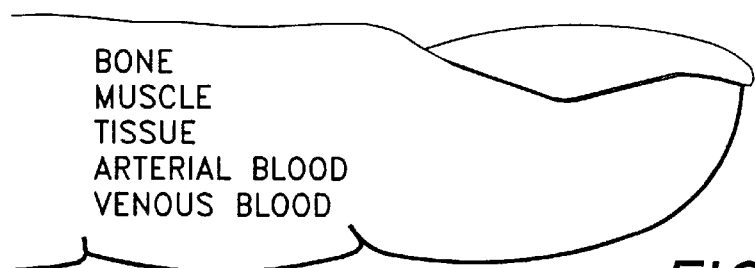
FIG. 2 schematically illustrates the cross-sectional structure of a typical finger.
Figure 3:
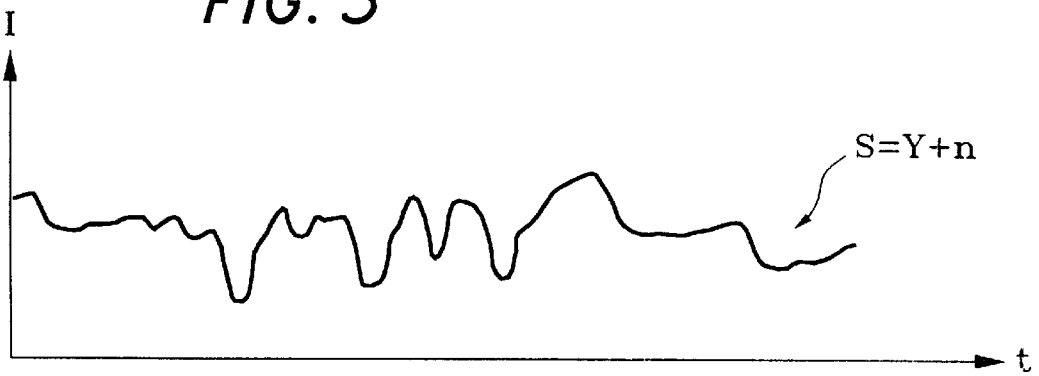
FIG. 3 illustrates a plethysmographic waveform which includes a motion-induced undesired erratic signal portion.
Figure 4:
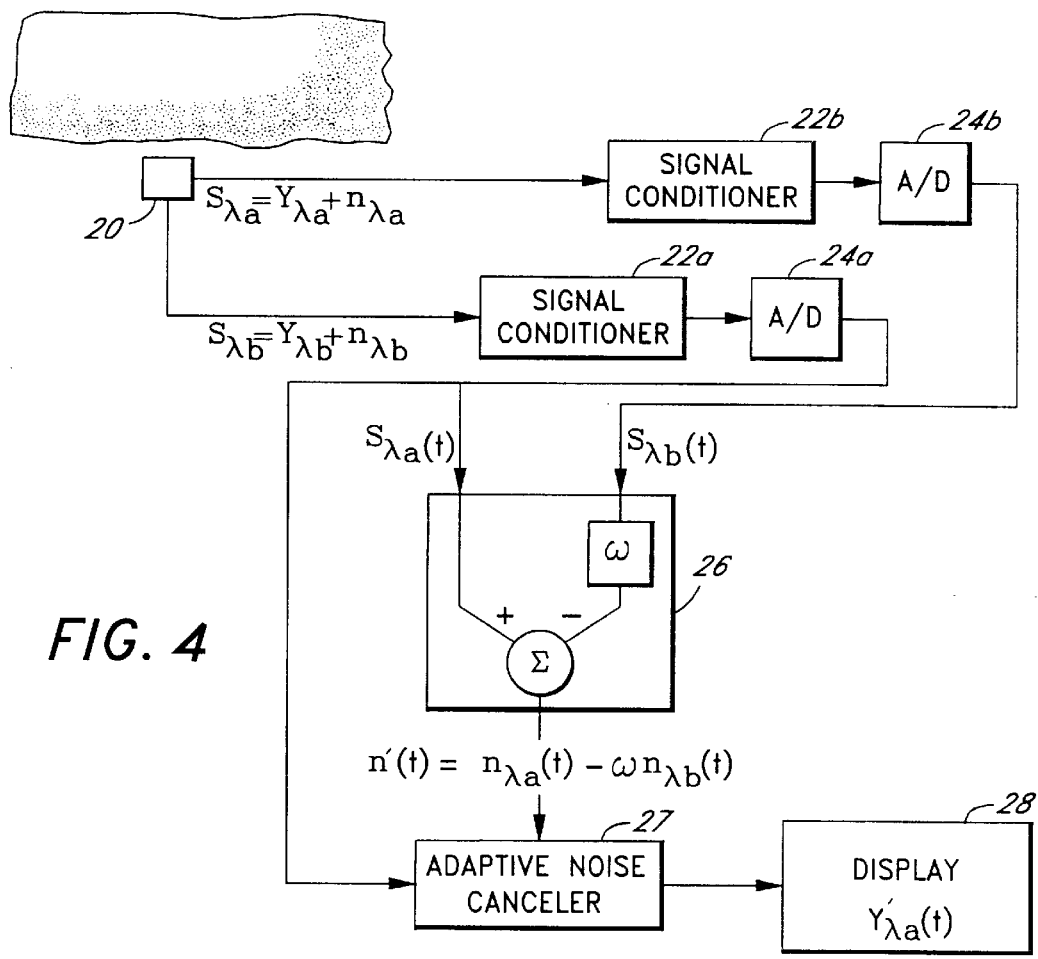
FIG. 4 illustrates a schematic diagram of a physiological monitor incorporating a processor of this present invention and an adaptive noise canceler.

A block diagram of a generic monitor incorporating at signal processor, or reference processor, according to the present invention and an adaptive noise canceler is shown in FIG. 4. Two measured signals, $S_{\lambda a}(t)$ and $S_{\lambda b}(t)$, are acquired by a detector 20. One skilled in the art will realize that for some physiological measurements, more than one detector may be advantageous. Each signal is conditioned by a signal conditioner 22a and 22b. Conditioning includes, but is not limited to, such procedures as filtering the signals to remove constant portions and amplifying the signals for ease of manipulation. The signals are then converted to digital data by an analog-to-digital converter 24a and 24b. The first measured signal $S_{\lambda a}(t)$ comprises at first desired signal portion, labelled herein $Y_{\lambda a}(t)$, and a first undesired signal portion, labelled herein $n_{\lambda a}(t)$. The second measured signal $S_{\lambda b}(t)$ is at least partially correlated to the first measured signal $S_{\lambda b}(t)$ and comprises a second desired signal portion, labelled herein $Y_{\lambda b}(t)$, and a second undesired signal portion, labelled herein $n_{\lambda b}(t)$. Typically the first and second undesired signal portions, $n_{\lambda a}(t)$ and $n_{\lambda b}(t)$, are uncorrelated and/or erratic with respect to the desired signal portions $Y_{\lambda a}(t)$ and $Y_{\lambda b}(t)$. The undesired signal portions $n_{\lambda a}(t)$ and $n_{\lambda b}(t)$ are often caused by motion of a patient. The signals $S_{\lambda a}(t)$ and $S_{\lambda b}(t)$ are input to a reference processor 26. The reference processor 26 multiplies the second measured signal $S_{\lambda b}(t)$ by a factor $\omega$ and then subtracts the second measured signal $S_{\lambda b}(t)$ from the first measured signal $S_{\lambda a}(t)$. The factor $\omega$ is determined to cause the desired signal portions $Y_{\lambda a}(t)$ and $Y_{\lambda b}(t)$ to cancel when the two signals $S_{\lambda a}(t)$ and $S_{\lambda b}(t)$ are subtracted. Thus, the output of the reference processor 26 is a noise reference signal n'(t)=$n_{\lambda a}(t)-\omega n_{\lambda b}(t)$ which is correlated to both of the erratic undesired signal portions $n_{\lambda a}(t)$ and $n_{\lambda b}(t)$. The noise reference signal n'(t) is input, along with one of the measured signals $S_{\lambda a}(t)$, to an adaptive noise canceler 27 which uses the noise reference signal n'(t) to remove the undesired signal portion $n_{\lambda a}(t)$ or $n_{\lambda b}(t)$ from the measured signal $S_{\lambda a}(t)$. It will be understood that $S_{\lambda b}(t)$ could have been input to the adaptive noise canceler 27 along with the noise reference signal n'(t) instead of $S_{\lambda a}(t)$. The output of the adaptive noise canceler 27 is a good approximation $Y'_{\lambda a}(t)$ to the desired signal $Y_{\lambda a}(t)$. The approximation $Y'_{\lambda a}(t)$ is displayed on the display 28.

An adaptive noise canceler 30, an example of which is shown in block diagram in FIG. 5, is employed to remove the erratic, undesired signal portions $n_{\lambda a}(t)$ and $n_{\lambda b}(t)$ from the measured signals $S_{\lambda a}(t)$ and $S_{\lambda b}(t)$. The adaptive noise canceler 30 in FIG. 5 has as one input a sample of the noise reference signal n'(t) which is correlated to the undesired signal portions $n_{\lambda a}(t)$ and $n_{\lambda b}(t)$. The noise reference signal n'(t) is determined from the two measured signals $S_{\lambda a}(t)$ and $S_{\lambda b}(t)$ by the processor 26 of the present invention as described herein. A second input to the adaptive noise canceler is a sample of either the first or second measured signal $S_{\lambda a}(t)=Y_{\lambda b}(t)+n_{\lambda a}(t)$ or $S_{\lambda b}(t)=Y_{\lambda b}(t)+n_{\lambda b}(t)$.

The adaptive noise canceler 30 functions to remove frequencies common to both the noise reference signal n'(t) and the measured signal $S_{\lambda a}(t)$ or $S_{\lambda b}(t)$. Since the noise reference signal n'(t) is correlated to the erratic undesired signal portions $n_{\lambda a}(t)$ and $n_{\lambda b}(t)$, the noise reference signal n'(t) is also erratic. The adaptive noise canceler acts in a manner which may be analogized to a dynamic multiple notch filter based on the spectral distribution of the noise reference signal n'(t).

Figure 4A:
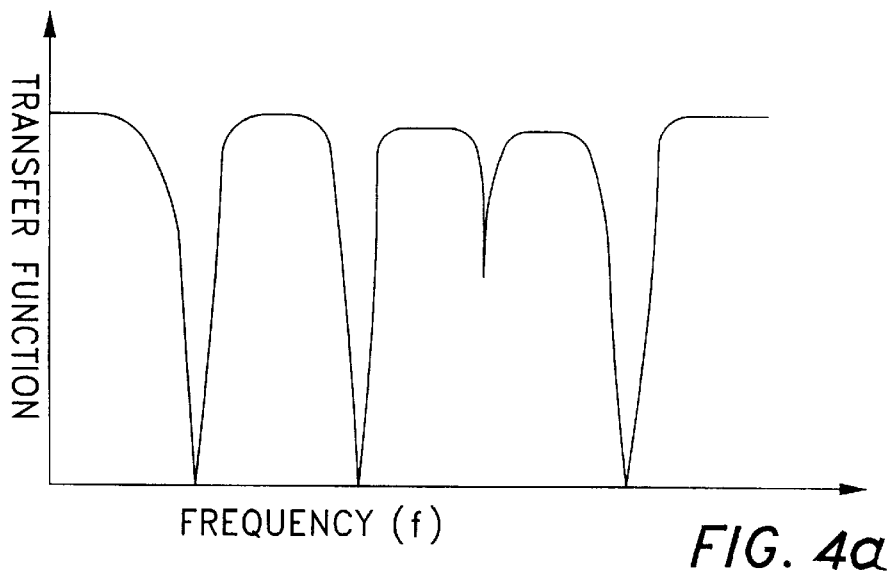
FIG. 4a illustrates the transfer function of a multiple notch filter.

Referring to FIG. 4a, the transfer function of a multiple notch filter is shown. The notches, or dips in the amplitude of the transfer function, indicate frequencies which are attenuated or removed when a composite measured signal passes through the notch filter. The output of the notch filter is the composite signal having frequencies at which a notch was present removed. In the analogy to an adaptive noise canceler, the frequencies at which notches are present change continuously based upon the inputs to the adaptive noise canceler.

The adaptive noise canceler 30 shown in FIG. 5 produces an output signal, labelled herein $Y'_{\lambda a}(t)$ or $Y'_{\lambda b}(t)$, which is fed back to an internal processor 32 within the adaptive noise canceler 30. The internal processor 32 automatically adjusts its own transfer function according to a predetermined algorithm such that the output of the internal processor 32, labelled b(t), closely resembles the undesired signal portion $n_{\lambda a}(t)$ or $n_{\lambda b}(t)$. The output b(t) of the internal processor 32 is subtracted from the measured signal, $S_{\lambda a}(t)$ or $S_{\lambda b}(t)$, yielding a signal $Y'_{\lambda a}(t) \approx S_{\lambda a}(t) + n_{\lambda a}(t) - b_{\lambda a}(t)$ or $Y'_{\lambda b}(t) \approx S_{\lambda b}(t) + n_{\lambda b}(t) - b_{\lambda b}(t)$. The internal processor optimizes $Y'_{\lambda a}(t)$ or $Y'_{\lambda b}(t)$ such that $Y'_{\lambda a}(t)$ or $Y'_{\lambda b}(t)$ is approximately equal to the desired signal $Y_{\lambda a}(t)$ or $Y_{\lambda b}(t)$, respectively.

One algorithm which may be used for the adjustment of the transfer function of the internal processor 32 is a least-squares algorithm, as described in Chapter 6 and Chapter 12 of the book *Adaptive Signal Processing* by Bernard Widrow and Samuel Stearns, published by Prentice Hall, copyright 1985. This entire book, including Chapters 6 and 12, is hereby incorporated herein by reference.

Adaptive processors in have been successfully applied to a number of problems including antenna sidelobe canceling, pattern recognition, the elimination of periodic interference in general, and the elimination of echoes on long distance telephone transmission lines. However, considerable ingenuity is often required to find a suitable noise reference signal n'(t) for a given application since the random or erratic portions $n_{\lambda a}(t)$ or $n_{\lambda b}(t)$ cannot easily be separated from the measured signal $S_{\lambda a}(t)$ or $S_{\lambda b}(t)$. If the actual undesired signal portion $n_{\lambda a}(t)$ or $n_{\lambda b}(t)$ were a priori available, techniques such as adaptive noise canceling would not be necessary. The unique determination of a suitable noise reference signal n'(t) from measurements taken by at monitor incorporating a reference processor of the present invention is one aspect of the present invention.

GENERALIZED DETERMINATION OF NOISE REFERENCE SIGNAL

An explanation which describes how the noise reference signal n'(t) may be determined as follows. A first signal is measured at, for example, a wavelength λa, by a detector yielding a signal $S_{\lambda a}(t)$:

$$S_{\lambda a}(t) = Y_{\lambda a}(t) + n_{\lambda a}(t); \tag{1}$$

where $Y_{\lambda a}(t)$ is the desired signal and $n_{\lambda a}(t)$ is the noise component.

A similar measurement is taken simultaneously, or nearly simultaneously, at a different wavelength, λb, yielding:

$$S_{\lambda b}(t) = Y_{\lambda b}(t) + n_{\lambda b}. \tag{2}$$

Note that as long as the measurements, $S_{\lambda a}(t)$ and $S_{\lambda b}(t)$, are taken substantially simultaneously, the undesired signal components, $n_{\lambda a}(t)$ and $n_{\lambda b}(t)$, will be correlated because any random or erratic functions will affect each measurement in nearly the same fashion.

To obtain the noise reference signal n'(t), the measured signals $S_{\lambda a}(t)$ and $S_{\lambda b}(t)$ are transformed to eliminate the desired signal components. One way of doing this is to find a proportionality constant, $\omega_1$, between the desired signals $Y_{\lambda a}(t)$ and $Y_{\lambda b}(t)$ such that:

$$Y_{\lambda a}(t) = \omega_1 Y_{\lambda b}(t). \tag{3}$$

This proportionality relationship can be satisfied in many measurements, including but not limited to absorption measurements and physiological measurements. Additionally, in most measurements, the proportionality constant $\omega_1$ can be determined such that:

$$n_{\lambda a}(t) \neq \omega_1 n_{\lambda b}(t). \tag{4}$$

Multiplying equation (2) by $\omega_1$ and then subtracting equation (2) from equation (1) results in a single equation wherein the desired signal terms $Y_{\lambda a}(t)$ and $S_{\lambda b}(t)$ cancel, leaving:

$$n'(t) = S_{\lambda a}(t) - \omega_1 S_{\lambda b}(t) = n_{\lambda a}(t) - \omega_1 n_{\lambda b}(t); \tag{5}$$

a non-zero signal which is correlated to each undesired signal portion $n_{\lambda a}(t)$ and $n_{\lambda b}(t)$ and can be used as the noise reference signal n'(t) in an adaptive noise canceler.

EXAMPLE OF DETERMINATION OF NOISE REFERENCE SIGNAL IN AN ABSORPTIVE SYSTEM

Adaptive noise canceling is particularly useful in a large number of measurements generally described as absorption measurements. An example of an absorption type monitor which can advantageously employ adaptive noise canceling based upon a noise reference signal n'(t) determined by a processor of the present invention is one which determines the concentration of an energy absorbing constituent within an absorbing material when the material is subject to perturbation. Such perturbations ran be caused by forces about which information is desired, or alternatively, by random or erratic forces such as a mechanical force on the material. Random or erratic interference, such as motion, generates undesired noise components in the measured signal. These undesired components can be removed by the adaptive noise canceler if a suitable noise reference signal n'(t) is known.

A schematic N constituent absorbing material comprising a container 42 having N different absorbing constituents, labelled $A_1, A_2, A_3, \ldots A_N$, is shown schematically in FIG. 6a. The constituents $A_1$ through $A_N$ in FIG. 6a are arranged in a generally orderly, layered fashion within the container 42. An example of a particular type of absorptive system is one in which light energy passes through the container 42 and is absorbed according to the generalized Beer-lambert Law or light absorption. For light of wavelength λa, this attenuation may be approximated by:

$$I = I_0 e^{-\sum_{i=0}^{N} \epsilon_{i,\lambda a} c_i x_i} \tag{6}$$

Initially transforming the signal by taking the natural log of both sides and manipulating terms, the signal is transformed such that the signal components are combined by addition rather than multiplication, i.e.:

$$S_{\lambda a} = \ln(I_0/I) = \sum_{i=0}^{N} \epsilon_{i,\lambda a} c_i x_i \tag{7}$$

where $I_0$ is the incident light energy intensity; I is the transmitted light energy intensity; $\epsilon_{1,\lambda a}$ is the absorption coefficient of the $i^{th}$ constituent at the wavelength λa; $x_i(t)$ is the optical path length of $i^{th}$ layer, i.e., the thickness of material of the $i^{th}$ layer through which optical energy passes; and $c_i(t)$ is the concentration of the it constituent in the volume associated with the thickness $x_i(t)$. The absorption coefficients $\epsilon_1$ through $\epsilon_N$ are known values which are constant at each wavelength. Most concentrations $c_1(t)$ through $c_N(t)$ are typically unknown, as are most of the optical path lengths $x_i(t)$ of each layer. The total optical path length is the sum of each of the individual optical path lengths $x_i(t)$ of each layer.

When the material is not subject to any forces which cause perturbation in the thicknesses of the layers, the optical path length of each layer, $x_i(t)$, is generally constant. This results in generally constant attenuation of the optical energy and thus, a generally constant offset in the measured signal. Typically, this portion of the signal is of little interest since knowledge about a force which perturbs the material is usually desired. Any signal portion outside of a known bandwidth of interest, including the constant undesired signal portion resulting from the generally constant absorption of the constituents when not subject to perturbation, should be removed. This is easily accomplished by traditional band pass filtering techniques. However, when the material is subject to forces, each layer of constituents may be affected by the perturbation differently than each other layer. Some perturbations of the optical path lengths of each layer $x_i(t)$ may result in excursions in the measured signal which represent desired information. Other perturbations of the optical path length of each layer $x_i(t)$ cause undesired excursions which mask desired information in the measured signal. Undesired signal components associated with undesired excursions must also be removed to obtain desired information from the measured signal.

The adaptive noise canceler removes from the composite signal, measured after being transmitted through or reflected from the absorbing material, the undesired signal components caused by forces which perturb the material differently from the forces which perturbed the material to cause the desired signal component. For the purposes of illustration, it will be assumed that the portion of the measured signal which is deemed the desired signal $Y_{\lambda a}(t)$ is the attenuation term $\epsilon_5 c_5 x_5(t)$ associated with a constituent of interest, namely $A_5$, and that the layer of constituent $A_5$ is affected by perturbations differently than each of the layers of other constituents $A_1$ through $A_4$ and $A_6$ through $A_N$. An example of such a situation is when layer $A_5$ is subject to forces about which information is desired and, additionally, the entire material is subject to forces which affect each of the layers. In this case, since the total force affecting the layer of constituents As is different than the total forces affecting each of the other layers and information is desired about the forces and resultant perturbation of the layer of constituents $A_5$, attenuation terms due to constituents $A_1$ through $A_4$ and $A_6$ through $A_N$ make up the undesired signal $n_{\lambda a}(t)$. Even if the additional forces which affect the entire material cause the same perturbation in each layer, including the layer of $A_5$, the total forces on the layer of constituent $A_5$ cause it to have different total perturbation than each of the other layers of constituents $A_1$ through $A_4$ and $A_6$ through $A_N$.

It is often the case that the total perturbation affecting the layers associated with the undesired signal components is caused by random or erratic forces. This causes the thickness of layers to change erratically and the optical path length of each layer, $x_i(t)$, to change erratically, thereby producing a random or erratic undesired signal component $n_{\lambda a}(t)$. However, regardless of whether or not the undesired signal portion $n_{\lambda a}(t)$ is erratic, the undesired signal component $n_{\lambda a}(t)$ can be removed via an adaptive noise canceler having as one input a noise reference signal n'(t) determined by a processor of the present invention as long as the perturbation on layers other than the layer of constituent $A_5$ is different than the perturbation on the layer of constituent $A_5$. The adaptive noise canceler yields a good approximation to the desired signal $Y'_{\lambda a}(t)$. From this approximation, the concentration of the constituent of interest, $c_5(t)$, can often be determined since in some physiological measurements, the thickness of the desired signal component, $x_5(t)$ in this example, is known or can be determined.

The adaptive noise canceler utilizes a sample of a noise reference signal n'(t) determined from two substantially simultaneously measured signals $S_{\lambda a}(t)$ and $S_{\lambda b}(t)$. $S_{\lambda a}(t)$ is determined as above in equation (7). $S_{\lambda b}(t)$ is determined similarly at a different wavelength $\lambda b$. To find the noise reference signal n'(t), attenuated transmitted energy is measured at the two different wavelengths $\lambda a$ and $\lambda b$ and transformed via logarithmic conversion. The signals $S_{\lambda a}(t)$ and $S_{\lambda b}(t)$ can then be written (logarithm converted) as:

$$S_{\lambda a}(t) = \epsilon_{5,\lambda a} c_5 x_5(t) + \left[\sum_{i=1}^{4} \epsilon_{i,\lambda a} c_i x_i(t) + \sum_{k=6}^{N} \epsilon_{k,\lambda a} c_k x_k(t)\right] \quad (8)$$

$$S_{\lambda b}(t) = \epsilon_{5,\lambda b} c_5 x_5(t) + \left[\sum_{i=1}^{4} \epsilon_{i,\lambda b} c_i x_i(t) + \sum_{k=6}^{N} \epsilon_{k,\lambda b} c_k x_k(t)\right] \quad (10)$$

A further transformation of the signals is the proportionality relationship defining $\omega_2$, similarly to equation (3), which allows determination of a noise reference signal n'(t), is:

$$\epsilon_{5,\lambda a} = \omega_2 \epsilon_{5,\lambda b}; \text{ where} \quad (12)$$

$$n_{\lambda a} \neq \omega_2 n_{\lambda b}. \quad (13)$$

It is often the case that both equations (12) and (13) can be simultaneously satisfied. Multiplying equation (11) by $\omega_2$ and subtracting the result from equation (9) yields a non-zero noise reference signal which is a linear sum of undesired signal components:

$$n'(t) = S_{\lambda a}(t) - \omega_2 S_{\lambda b}(t) = n_{\lambda a}(t) - \omega_2 n_{\lambda b}(t). \quad (14)$$

$$= \sum_{i=1}^{4} \epsilon_{i,\lambda a} c_i x_i(t) + \sum_{k=6}^{N} \epsilon_{k,\lambda a} c_k x_k(t) - \quad (15)$$
$$\sum_{i=1}^{4} \omega_2 \epsilon_{i,\lambda b} c_i x_i(t) - \sum_{k=6}^{N} \omega_2 \epsilon_{k,\lambda b} c_k x_k(t)$$

$$= \sum_{i=1}^{4} c_i x_i(t) [\epsilon_{i,\lambda a} - \omega_2 \epsilon_{i,\lambda b}] + \sum_{k=6}^{N} c_k x_k(t) [\epsilon_{k,\lambda a} - \omega_2 \epsilon_{k,\lambda b}] \quad (16)$$

A sample of this noise reference signal n'(t), and a sample of either measured signal $S_{\lambda a}(t)$ or $S_{\lambda b}(t)$, are input to an adaptive noise canceler, one model of which is shown in FIG. 5 and a preferred model of which is discussed herein under the heading PREFERRED ADAPTIVE NOISE CANCELER USING A JOINT PROCESS ESTIMATOR IMPLEMENTATION. The adaptive noise canceler removes the undesired portion of the measured signal $n_{\lambda a}(t)$ or $n_{\lambda b}(t)$, yielding a good approximation to the desired portion of signal $Y'_{\lambda a}(t) \approx \epsilon_{5,\lambda a} c_5 x_5(t)$ or $Y'_{\lambda b}(t) \approx \epsilon_{5,\lambda b} c_{5,x5}(t)$. The concentration $c_5(t)$ may then be determined from the approximation to the desired signal $Y'_{\lambda a}(t)$ or $Y'_{\lambda b}(t)$ according to:

$$c_5(t) \approx Y'_{\lambda a}(t) / \epsilon_{5,\lambda a} x_5(t) \approx Y'_{\lambda b}(t) / \epsilon_{5,\lambda b} x_5(t). \quad (17)$$

As discussed previously, the absorption coefficients are constant at each wavelength $\lambda a$ and $\lambda b$ and the thickness of the desired signal component, $x_5(t)$ in this example, is often known or can be determined as a function of time, thereby allowing calculation of the concentration $c_5(t)$ of constituent $A_5$.

DETERMINATION OF CONCENTRATION OR SATURATION IN A VOLUME CONTAINING MORE THAN ORE CONSTITUENT

Referring to FIG. 6b, another material having N different constituents arranged in layers is shown. In this material, two constituents $A_5$ and $A_6$ are found within one layer having thickness $x_{5,6}(t)=x_5(t)+x_6(t)$, located generally randomly within the layer. This is analogous to combining the layers of constituents $A_5$ and $A_6$ in FIG. 6a. A combination of layers, such as the combination of layers of constituents $A_5$ and $A_6$, is feasible when the two layers are under the same total forces which result in the same perturbation of the optical path lengths $x_5(t)$ and $x_6(t)$ of the layers.

Often it is desirable to find the concentration or the saturation, i.e., a percent concentration, of one constituent within a given thickness which contains more than one constituent and is subject to unique forces. A determination of the concentration or the saturation of a constituent within a given volume may be made with any number of constituents in the volume subject to the same total forces and therefore under the same perturbation. To determine the saturation of one constituent in a volume comprising many constituents, as many measured signals as there are constituents which absorb incident light energy are necessary. It will be understood that constituents which do not absorb light energy are not consequential in the determination of saturation. To determine the concentration as many signals as there are constituents which absorb incident light energy are necessary as well as information about the sum of concentrations.

It is often the case that a thickness under unique motion contains only two constituents. For example, it may be desirable to know the concentration or saturation of $A_5$ within a given volume which contains $A_5$ and $A_6$. In this case, the desired signals $Y_{\lambda a}(t)$ and $Y_{\lambda b}(t)$ comprise terms related to both $A_5$ and $A_6$ so that a determination of the concentration or saturation of $A_5$ or $A_6$ in the volume may be made. A determination of saturation is discussed herein. It will bet understood that the concentration of $A_5$ in volume containing both $A_5$ and $A_6$ could also be determined if it is known that $A_5+A_6=1$, i.e., that there are no constituents in the volume which do not absorb incident light energy at the particular measurement wavelengths chosen. The measured signals $S_{\lambda a}(t)$ and $S_{\lambda b}(t)$ can be written (logarithm converted) as:

$$S_{\lambda a}(t)=\epsilon_{5,\lambda a}c_5 x_{5,6}(t)+\epsilon_{6,\lambda a}c_6 x_{5,6}(t)+n_{\lambda a}(t) \quad (18)$$

$$=Y_{\lambda a}(t)+n_{\lambda a}(t); \quad (19)$$

$$S_{\lambda b}(t)=\epsilon_{5,\lambda b}c_5 x_{5,6}(t)+\epsilon_{6,\lambda b}c_6 x_{5,6}(t)+n_{\lambda b}(t) \quad (20)$$

$$=Y_{\lambda b}(t)+n_{\lambda b}(t). \quad (21)$$

Any signal portions outside of a known bandwidth of interest, including the constant undesired signal portion resulting from the generally constant absorption of the constituents when not under perturbation, should be removed to determine an approximation to the desired signal. This is easily accomplished by traditional band pass filtering techniques. As in the previous example, it is often the case that the total perturbation affecting the layers associated with the undesired signal components is caused by random or erratic forces, causing the thickness of each layer, or the optical path length of each layer, $x_1(t)$, to change erratically, producing a random or erratic undesired signal component $n_{\lambda a}(t)$. Regardless of whether or not the undesired signal portion $n_{\lambda a}(t)$ is erratic, the undesired signal component $n_{\lambda a}(t)$ can be removed via an adaptive noise canceler having as one input a noise reference signal n'(t) determined by a processor of the present invention as long as the perturbation in layers other than the layer of constituents $A_5$ and $A_6$ is different than the perturbation in the layer of constituents $A_5$ and $A_6$. The erratic undesired signal components $n_{\lambda a}(t)$ and $n_{\lambda b}(t)$ may advantageously be removed from equations (18) and (20), or alternatively equations (19) and (21), by an adaptive noise canceler. The adaptive noise canceler, again, requires a sample of a noise reference signal n'(t).

DETERMINATION OF NOISE REFERENCE SIGNAL FOR SATURATION MEASUREMENT

Two methods which may be used by a processor of the present invention to determine the noise reference signal n'(t) are a ratiometric method and a constant saturation method. The preferred embodiment of a physiological monitor incorporating a processor of the present invention utilizes the ratiometric method wherein the two wavelengths $\lambda a$ and $\lambda b$, at which the signals $S_{\lambda a}(t)$ and $S_{\lambda b}(t)$ are measured, are specifically chosen such that a relationship between the absorption coefficients $\epsilon_{5,\lambda a}$, $\epsilon_{5,\lambda b}$, $\epsilon_{6,\lambda a}$ and $\epsilon_{6,\lambda b}$ exists, i.e.:

$$\epsilon_{5,\lambda a}/\epsilon_{6,\lambda a}=\epsilon_{5,\lambda b}/\epsilon_{6,\lambda b} \quad (22)$$

The measured signals $S_{\lambda a}(t)$ and $S_{\lambda b}(t)$ can be factored and written as:

$$S_{\lambda a}(t)=\epsilon_{6,\lambda a}[(\epsilon_{5,\lambda a}/\epsilon_{6,\lambda a})c_5 x(t)]+n_{\lambda a}(t) \quad (23)$$

$$S_{\lambda b}(t)=\epsilon_{6,\lambda b}[(\epsilon_{5,\lambda b}/\epsilon_{6,\lambda b})c_5 x(t)+c_6 x(t)]+n_{\lambda b}(t) \quad (24)$$

The wavelengths $\lambda a$ and $\lambda b$, chosen to satisfy equation (22), cause the terms within the square brackets to be equal, thereby causing the desired signal portions $Y'_{\lambda a}(t)$ and $Y'_{\lambda b}(t)$ to be linearly dependent. Then, a proportionality constant $\omega_{r3}$ which causes the desired signal portions $Y'_{\lambda a}(t)$ and $Y'_{\lambda b}(t)$ to be equal and allows determination of a non-zero noise reference signal n'(t) is:

$$\epsilon_{6,\lambda a}=\omega_{r3}\epsilon_{6,\lambda b}; \text{ where} \quad (25)$$

$$n_{\lambda a} \neq \omega_{r3} n_{\lambda b}. \quad (26)$$

It is often the case that both equations (25) and (26) can be simultaneously satisfied. Additionally, since absorption coefficients of each constituent are constant with respect to wavelength, the proportionality constant $\omega_{r3}$ can be easily determined. Furthermore, absorption coefficients of other constituents $A_1$ through $A_4$ and $A_7$ through $A_N$ are generally unequal to the absorption coefficients of $A_5$ and $A_6$. Thus, the undesired noise components $n_{\lambda a}$ and $n_{\lambda b}$ are generally not made linearly dependent by the relationships of equations (22) and (25).

Multiplying equation (24) by $\omega_{r3}$ and subtracting the resulting equation from equation (23), a non-zero noise reference signal is determined by:

$$n'(t)=S_{\lambda a}(t)-\omega_{r3}S_{\lambda b}(t)=n_{\lambda a}(t)-\omega_{r3}n_{\lambda b}(t). \quad (27)$$

An alternative method for determining the noise reference signal from the measured signals $S_{\lambda a}(t)$ and $S_{\lambda b}(t)$ using a processor of the present invention is the constant saturation approach. In this approach, it is assumed that the saturation of $A_5$ in the volume containing $A_5$ and $A_6$ remains relatively constant, i.e.:

$$\text{Saturation}(A_5(t)) = c_5(t)/[c_5(t)+c_6(t)] \quad (28)$$

$$= \{1+[c_6(t)/c_5(t)]\}^{-1} \quad (29)$$

is substantially constant over many samples of the measured signals $S_{\lambda a}$ and $S_{\lambda b}$. This assumption is accurate over many samples since saturation generally changes relatively slowly in physiological systems.

The constant saturation assumption is equivalent to assuming that:

$$c_5(t)/c_6(t) = \text{constant} \quad (30)$$

since the only other term in equation (29) is a constant, namely the numeral 1.

Using this assumption, the proportionality constant $\omega_{a3}(t)$ which allows determination of the noise reference signal n'(t) is:

$$\omega_{a3}(t) = \frac{\epsilon_{5,\lambda a} c_5 x_{5,6}(t) + \epsilon_{6,\lambda a} c_6 x_{5,6}(t)}{\epsilon_{5,\lambda b} c_5 x_{5,6}(t) + \epsilon_{6,\lambda b} c_6 x_{5,6}(t)} \quad (31)$$

$$= Y_{\lambda a}(t)/Y_{\lambda b}(t) \quad (32)$$

$$= \frac{\epsilon_{5,\lambda a} c_5 + \epsilon_{6,\lambda a} c_6}{\epsilon_{5,\lambda b} c_5 + \epsilon_{6,\lambda b} c_6} \quad (33)$$

$$= \frac{\epsilon_{5,\lambda a}\left(\frac{c_5(t)}{c_6(t)}\right) + \epsilon_{6,\lambda a}}{\epsilon_{5,\lambda b}\left(\frac{c_5(t)}{c_6(t)}\right) + \epsilon_{6,\lambda b}} \quad (34)$$

$$\approx Y'_{\lambda a}(t)/Y'_{\lambda b}(t) = \text{constant; where} \quad (35)$$

$$n_{\lambda a}(t) \neq \omega_{a3}(t) n_{\lambda b}(t). \quad (36)$$

It is often the case that both equations (35) and (36) can be simultaneously satisfied to determine the proportionality constant $\omega_{a3}(t)$. Additionally, the absorption coefficients at each wavelength $\epsilon_{5,\lambda a}$, $\epsilon_{6,\lambda a}$, $\epsilon_{5,\lambda b}$, and $\epsilon_{6,\lambda b}$ are constant and the central assumption of the constant saturation method is that $c_5(t)/c_6(t)$ is constant over many sample periods. Thus, a new proportionality constant $\omega_{a3}(t)$ may be determined every few samples from new approximations to the desired signal a; output from the adaptive noise canceler. Thus, the approximations to the desired signals $Y'_{\lambda a}(t)$ and $Y'_{\lambda b}(t)$, found by the adaptive noise canceler for a substantially immediately preceding set of samples of the measured signals $S_{\lambda a}(t)$ and $S_{\lambda b}(t)$ are used in a processor of the present invention for calculating the proportionality constant, $\omega_{a3}(t)$, for the next set of samples of the measured signals $S_{\lambda a}(t)$ and $S_{\lambda b}(t)$.

Multiplying equation (20) by $\omega_{a3}(t)$ and subtracting the resulting equation from equation (18) yields a non-zero noise reference signal:

$$n'(t) = S_{\lambda a}(t) - \omega_{a3}(t) S_{\lambda b}(t) = n_{\lambda a}(t) - \omega_{a3}(t) n_{\lambda b}(t). \quad (37)$$

It will be understood that equation (21) could be multiplied by $\omega_{c3}(t)$ and the resulting equation could be subtracted from equation (19) to yield the same noise reference signal n'(t) as given in equation (37).

When using the constant saturation method, it is necessary for the patient to remain motionless for a short period of time such that an accurate initial saturation value can be determined by known methods other than adaptive noise canceling on which all other calculations will be based. With no erratic, motion-induced undesired signal portions, a physiological monitor can very quickly produce an initial value of the saturation of $A_5$ in the volume containing $A_5$ and $A_6$. An example of a saturation calculation is given in the article "SPECTROPHOTOMETRIC DETERMINATION OF OXYGEN SATURATION OF BLOOD INDEPENDENT OF THE PRESENT OF INDOCYANINE GREEN" by G. A. Mook, et al., wherein determination of oxygen saturation in arterial blood is discussed. Another article discussing the calculation of oxygen saturation is "PULSE OXIMETRY: PHYSICAL PRINCIPLES, TECHNICAL REALIZATION AND PRESENT LIMITATIONS" by Michael R. Neuman. Then, with values for $Y'_{\lambda a}(t)$ and $Y'_{\lambda b}(t)$ determined, an adaptive noise canceler may be utilized with a noise reference signal n'(t) determined by the constant saturation method.

PREFERRED ADAPTIVE NOISE CANCELER USING A JOINT PROCESS ESTIMATOR IMPLEMENTATION

Once the noise reference signal n'(t) is determined by the processor of the present invention using either the above described ratiometric or constant saturation methods, the adaptive noise canceler can be implemented in either hardware or software.

The least mean squares (LMS) implementation of the internal processor 32 described above in conjunction with the adaptive noise canceler of FIG. 5 is relatively easy to implement, but lacks the speed of adaptation desirable for most physiological monitoring applications of the present invention. Thus, a faster approach for adaptive noise canceling, called a least-squares lattice joint process estimator model, is preferably used. A joint process estimator 60 is shown diagrammatically in FIG. 7 and is described in detail in Chapter 9 of *Adaptive Filter Theory* by Simon Haykin, published by Prentice-Hall, copyright 1986. This entire book, including Chapter 9, is hereby incorporated herein by reference. The function of the joint process estimator is to remove the undesired signal portions $n_{\lambda a}(t)$ or $n_{\lambda b}(t)$ from the measured signals $S_{\lambda a}(t)$ or $S_{\lambda b}(t)$, yielding a signal $Y'_{\lambda a}(t)$ or $Y'_{\lambda b}(t)$ which is a good approximation to the desired signal $Y_{\lambda a}(t)$ or $Y_{\lambda b}(t)$. Thus, the joint process estimator estimates the value of the desired signal $Y_{\lambda a}(t)$ or $Y_{\lambda b}(t)$. The inputs to the joint process estimator 60 are the noise reference signal n'(t) and the composite measured signal $S_{\lambda a}(t)$ or $S_{\lambda b}(t)$. The output is a good approximation to the signal $S_{\lambda a}(t)$ or $S_{\lambda b}(t)$ with the noise removed, i.e. a good approximation to $Y_{\lambda a}(t)$ or $Y_{\lambda b}(t)$.

The joint process estimator 60 utilizes, in conjunction, a least square lattice predictor 70 and a regression filter 80. The noise reference signal n'(t) is input to the least square lattice predictor 70 while the measured signal $S_{\lambda a}(t)$ or $S_{\lambda b}(t)$ is input to the regression filter 80. For simplicity in the following description, $S_{\lambda a}(t)$ will be the measured signal from which the desired portion $Y_{\lambda a}(t)$ will be estimated by the joint process estimator 60. However, it will be noted that $S_{\lambda b}(t)$ could equally well be input to the regression filter 80 and the desired portion $Y_{\lambda b}(t)$ of this signal could equally well be estimated.

The joint process estimator 60 removes all frequencies that are present in both the noise reference signal n'(t) and the measured signal $S_{\lambda a}(t)$. The undesired signal portion $n_{\lambda a}(t)$ usually comprises frequencies unrelated to those of the desired signal portion $Y_{\lambda a}(t)$. It is highly improbable that the undesired signal portion $n_{\lambda a}(t)$ would be of exactly the same spectral content as the desired signal portion $Y_{\lambda a}(t)$. However, in the unlikely event that the spectral content of $S_{\lambda a}(t)$ and n'(t) are similar, this approach will not yield accurate results. Functionally, the joint process estimator 60 compares input signal n'(t), which is correlated to the undesired signal portion $n_{\lambda a}(t)$, and input signal $S_{\lambda a}(t)$ and removes all frequencies which are identical. Thus, the joint process estimator 60 acts as a dynamic multiple notch filter to remove those frequencies in the undesired signal component $n_{\lambda a}(t)$ as they change erratically with the motion of the patient. This yields a signal having substantially the same spectral content as the desired signal $Y_{\lambda a}(t)$. The output of the joint process estimator 60 has substantially the same spectral content and amplitude as the desired signal $Y_{\lambda a}(t)$. Thus, the output $Y'_{\lambda a}(t)$ of the joint process estimator 60 is a very good approximation to the desired signal $Y_{\lambda a}(t)$.

Figure 7:
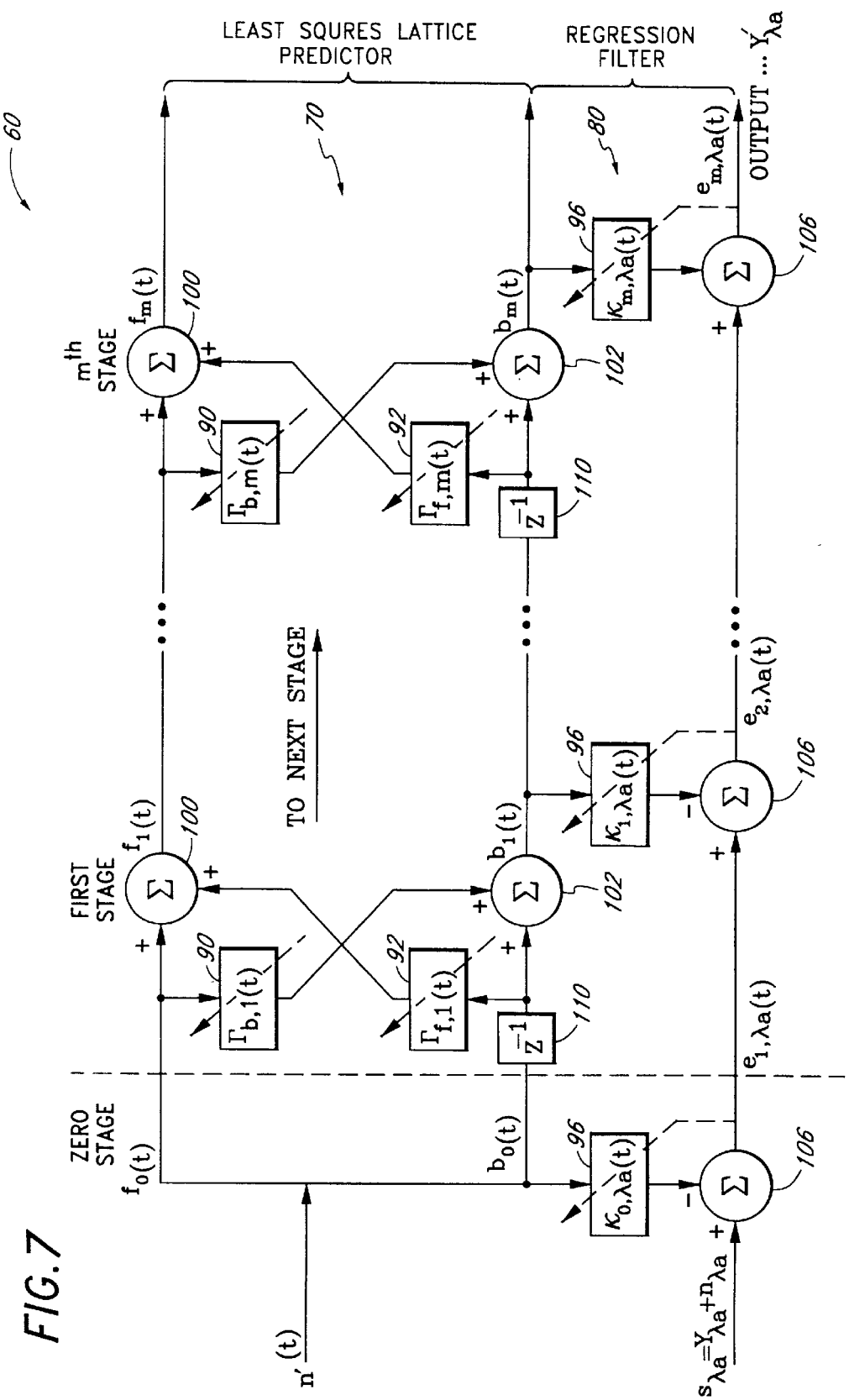
FIG. 7 is a schematic model of a joint process estimator comprising a least-squares lattice predictor and a regression filter.

The joint process estimator 60 can be divided into stages, beginning with a zero-stage and terminating in an $m^{th}$ stage, as shown in FIG. 7. Each stage, except for the zero-stage, is identical to every other stage. The zero-stage is an input stage for the joint process estimator 60. The first stage through the $m^{th}$-stage work on the signal produced in the immediately previous stage, i.e., the $(m-1)^{th}$-stage, such that a good approximation to the desired signal $Y'_{\lambda a}(t)$ is produced as output from the $m^{th}$-stage.

The least-squares lattice predictor 70 comprises registers 90 and 92, summing elements 100 and 102, and delay elements 110. The registers 90 and 92 contain multiplicative values of a forward reflection coefficient $\Gamma_{b,m}(t)$ and a backward reflection coefficient n'(t) which multiply the noise reference signal n'(t) and signals derived from the noise reference signal n'(t). Each stage of the least-squares lattice predictor outputs a forward prediction error $f_m(t)$ and a backward prediction error $b_m(t)$. The subscript m is indicative of the stage.

For each set of samples, i.e. one sample of the noise reference signal n'(t) derived substantially simultaneously with one sample of the measured signal $S_{\lambda a}(t)$, the sample of the noise reference signal n'(t) is input to the least-squares lattice predictor 70. The zero-stage forward prediction error $f_0(t)$ and the zero-stage backward prediction error $b_0(t)$ are set equal to the noise reference signal n'(t). The backward prediction error $b_0(t)$ is delayed by one sample period by the delay element 110 in the first stage of the least-squares lattice predictor 70. Thus, the immediately previous value of the noise reference signal n'(t) is used in calculations involving the first-stage delay element 110. The zero-stage forward prediction error is added to the negative of the delayed zero-stage backward prediction error $b_0(t-1)$ multiplied by the forward reflection coefficient value $\Gamma_{f,1}(t)$ register 90 value, to produce a first-stage forward prediction error $f_1(t)$. Additionally, the zero-stage forward prediction error $f_1(t)$ is multiplied by the backward reflection coefficient value $\Gamma_{b,1}(t)$ register 92 value and added to the delayed zero-stage backward prediction error $b_0(t-1)$ to produce a first-stage backward prediction error $b_1(t)$. In each subsequent stage, m, of the least square lattice predictor 70, the previous forward and backward prediction error values, $f_{m-1}(t)$ and $b_{m-1}(t-1)$, the backward prediction error being delayed by one sample period, are used to produce values of the forward and backward prediction errors for the present stage, $f_m(t)$ and $b_m(t)$.

The backward prediction error $b_m(t)$ is fed to the concurrent stage, m, of the regression filter 80. There it is input to a register 96, which contains a multiplicative regression coefficient value $\kappa_{m,\lambda a}(t)$. For example, in the zero-stage of the regression filter 80, the zero-stage backward prediction error $b_0(t)$ is multiplied by the zero-stage regression coefficient $\kappa_{0,\lambda a}(t)$ register 96 value and subtracted from the measured value of the signal $S_{\lambda a}(t)$ at a summing element 106 to produce a first stage estimation error signal $e_{1,\lambda a}(t)$.

The first-stage estimation error signal $e_{1,\lambda a}(t)$ is a first approximation to the desired signal. This first-stage estimation error signal $e_{1,\lambda a}(t)$ is input to the first-stage of the regression filter 80. The first-stage backward prediction error $b_1(t)$, multiplied by the first-stage regression coefficient $\kappa_{1,\lambda a}(t)$ register 96 value is subtracted from the first-stage estimation error signal $e_{1,\lambda a}(t)$ to produce the second-stage estimation error $e_{2,\lambda a}(t)$. The second-stage estimation error signal $e_{2,\lambda a}(t)$ is a second, somewhat better approximation to the desired signal $Y_{\lambda a}(t)$.

The same processes are repeated in the least-squares lattice predictor 70 and the regression filter 80 for each stage until a good approximation to the desired signal $Y'_{\lambda a}(t)=e_{m,\lambda a}(t)$ is determined. Each of the signals discussed above, including the forward prediction error $f_m(t)$, the backward prediction error $b_m(t)$, the estimation error signal $e_{m,\lambda a}(t)$, is necessary to calculate the forward reflection coefficient $\Gamma_{f,m}(t)$, the backward reflection coefficient $\Gamma_{b,m}(t)$, and the regression coefficient $\kappa_{m,\lambda a}(t)$ register 90, 92, and 96 values in each stage, m. In addition to the forward prediction error $f_m(t)$, the backward prediction error $b_m(t)$, and the estimation error $e_{m,\lambda a}(t)$ signals, a number of intermediate variables, not shown in FIG. 7 but based on the values labelled in FIG. 7, are required to calculate the forward reflection coefficient $\Gamma_{f,m}(t)$, the backward reflection coefficient $\Gamma_{b,m}(t)$, and the regression coefficient $\kappa_{m,\lambda a}(t)$ register 90,92, and 96 values.

Intermediate variables include a weighted sum of the forward prediction error squares $\Im_m(t)$, a weighted sum of the backward prediction error squares $\beta_m(t)$, a scaler parameter $\Delta_m(t)$, a conversion factor $\gamma_m(t)$, and another scaler parameter $\rho_{m,\lambda a}(t)$. The weighted sum of the forward prediction errors $\Im_m(t)$ is defined as:

$$\mathcal{F}_m(t) = \sum_{i=1}^{t} \lambda^{t-i} |f_m(i)|^2; \tag{38}$$

where λ without a wavelength identifier, a or b, is a constant multiplicative value unrelated to wavelength and is typically less than or equal to one, i.e., $\lambda \leq 1$. The weighted sum of the backward prediction errors $\beta_m(t)$ is defined as:

$$\beta_m(t) = \sum_{i=1}^{t} \lambda^{t-i} |b_m(i)|^2 \tag{39}$$

where, again, λ without a wavelength identifier, a or b, is a constant multiplicative value unrelated to wavelength and is typically less than or equal to one, i.e., $\lambda \leq 1$. These weighted sum intermediate error signals can be manipulated such that they are more easily solved for, as described in Chapter 9, § 9.3. And defined hereinafter in equations (53) and (54).

DESCRIPTION OF THE JOINT PROCESS ESTIMATOR

The operation of the joint process estimator 60 is as follows. When the joint process estimator 60 is turned on, the initial values of intermediate variable and signal including the parameter $\Delta_{m-1}(t)$, the weighted sum of the forward prediction error signals $\Im_{m-1}(t)$, the weighted sum of the backward prediction error signals $\beta_{m-1}(t)$, the parameter $\rho_{m,\lambda a}(t)$, and the zero-stage estimation error $e_{0,\lambda a}(t)$ are initialized, some to zero and some to a small positive number δ:

$$\Delta_{m-1}(0)=0; \qquad (40)$$

$$\Im_{m-1}(0)=\delta; \qquad (41)$$

$$\beta_{m-1}(0)=\delta; \qquad (42)$$

$$\rho_{m,\lambda a}(0)=0; \qquad (43)$$

$$e_{0,\lambda a}(t)=S_{\lambda a}(t) \text{ for } t\geq 0. \qquad (44)$$

After initialization, a simultaneous sample of the measured signal $S_{\lambda a}(t)$ and the noise reference signal $n'(t)$ are input to the joint process estimator 60, as shown in FIG. 7. The forward and backward prediction error signals $f_0(t)$ and $b_0(t)$, and intermediate variables including the weighted sums of the forward and backward error signals $\Im_0(t)$ and $\beta_0(t)$, and the conversion factor $\gamma_0(t)$ are calculated for the zero-stage according to:

$$f_0(t)=b_0(t)=n'(t) \qquad (45)$$

$$\Im_0(t)=\beta_0(t)=\lambda\Im_0(t-1)+|n'(t)|^2 \qquad (46)$$

$$\gamma_0(t-1)=1 \qquad (47)$$

where, again, $\lambda$ without a wavelength identifier, a or b, is a constant multiplicative value unrelated to wavelength.

Forward reflection coefficient $\Gamma_{f,m}(t)$, backward reflection coefficient $\Gamma_{b,m}(t)$, and regression coefficient $\kappa_{m,\lambda a}(t)$ register 90, 92 and 96 values in each stage thereafter are set according to the output of the previous stage. The forward reflection coefficient $\Gamma_{f,1}(t)$, backward reflection coefficient $\Gamma_{b,1}(t)$, and regression coefficient $\kappa_{1,\lambda a}(t)$ register 90, 92 and 96 values in the first stage are thus set according to algorithm using values in the zero-stage of the joint process estimator 60. In each stage, $m\geq 1$, intermediate values and register values including the parameter $\Delta_{m-1}(t)$; the forward reflection coefficient $\Gamma_{f,m}(t)$ register 90 value; the backward reflection coefficient $\Gamma_{b,m}(t)$ register 92 value; the forward and backward error signals $f_m(t)$ and $b_m(t)$; the weighted sum of squared forward prediction errors $\Im_{f,m}(t)$, as manipulated in § 9.3 of the Haykin book; the weighted sum of squared backward prediction errors $\beta_{b,m}(t)$, as manipulated in § 9.3 of the Haykin book; the conversion factor $\gamma_m(t)$; the parameter $\rho_{m,\lambda a}(t)$; the regression coefficient $\kappa_{m+1,\lambda a}(t)$ register 96 value; and the estimation error $e_{m+1,\lambda a}(t)$ value are set according to:

$$\Delta_{m-1}(t)=\lambda\Delta_{m-1}(t-1)+\{b_{m-1}(t-1)f^*_{m-1}(t)/\gamma_{m-1}(t-1)\} \qquad (48)$$

$$\Gamma_{f,m}(t)=-\{\Delta_{m-1}(t)/\beta_{m-1}(t-1)\} \qquad (49)$$

$$\Gamma_{b,m}(t)=-\{\Delta^*_{m-1}(t)/\Im_{m-1}(t)\} \qquad (50)$$

$$f_m(t)=f_{m-1}(t)+\Gamma^*_{f,m}(t)b_{m-1}(t-1) \qquad (51)$$

$$b_m(t)=b_{m-1}(t-1)+\Gamma^*_{b,m}(t)f_{m-1}(t) \qquad (52)$$

$$\Im_m(t)=\Im_{m-1}(t)-\{|\Delta_{m-1}(t)|^2/\beta_{m-1}(t-1)\} \qquad (53)$$

$$\beta_m(t)=\beta_{m-1}(t-1)-\{|\Delta_{m-1}(t)|^2/\Im_{m-1}(t)\} \qquad (54)$$

$$\gamma_m(t-1)=\gamma_{m-1}(t-1)-\{|b_{m-1}(t-1)|^2/\beta_{m-1}(t-1)\} \qquad (55)$$

$$\rho_{m,\lambda a}(t)=\lambda\rho_{m,\lambda a}(t-1)+\{b_m(t)e^*_{m,\lambda a}(t)/\gamma_m(t)\} \qquad (56)$$

$$\kappa_{m,\lambda a}(t)=\{\rho_{m,\lambda a}(t)/\beta_m(t)\} \qquad (57)$$

$$e_{m+1,\lambda a}(t)=e_{m,\lambda a}(t)-\kappa^*_m(t)b_m(t) \qquad (58)$$

where a (*) denotes a complex conjugate.

These equations cause the error signals $f_m(t)$, $b_m(t)$, $e_{m,\lambda a}(t)$ to be squared or to be multiplied by one another, in effect squaring the errors, and creating new intermediate error values, such as $\Delta_{m-1}(t)$. The error signals and the intermediate error values are recursively tied together, as shown in the above equations (48) through (58). They interact to minimize the error signals in the next stage.

After a good approximation to the desired signal $Y'_{\lambda a}(t)$ has been determined by the joint process estimator 60, a next set of samples, including a sample of the measured signal $S_{\lambda a}(t)$ and a sample of the noise reference signal $n'(t)$, are input to the joint process estimator 60. The re-initialization process does not re-occur, such that the forward and backward reflection coefficient $\Gamma_{f,m}(t)$ and $\Gamma_{b,m}(t)$ register 90, 92 values and the regression coefficient $\kappa_{m,\lambda a}(t)$ register 96 value reflect the multiplicative values required to estimate the desired portion $Y_{\lambda a}(t)$ of the sample of $S_{\lambda a}(t)$ input previously. Thus, information from previous samples is used to estimate the desired signal portion of a present set of samples in each stage.

FLOWCHART OF JOINT PROCESS ESTIMATOR

In a signal processor, such as a physiological monitor, incorporating a reference processor of the present invention to determine a noise reference signal $n'(t)$ for input to an adaptive noise canceler, a joint process estimator 60 type adaptive noise canceler is generally implemented via a software program having an iterative loop. One iteration of the loop is analogous to a single stage of the joint process estimator as shown in FIG. 7. Thus, if a loop is iterated m times, it is equivalent to an m stage joint process estimator 60.

Figure 8:
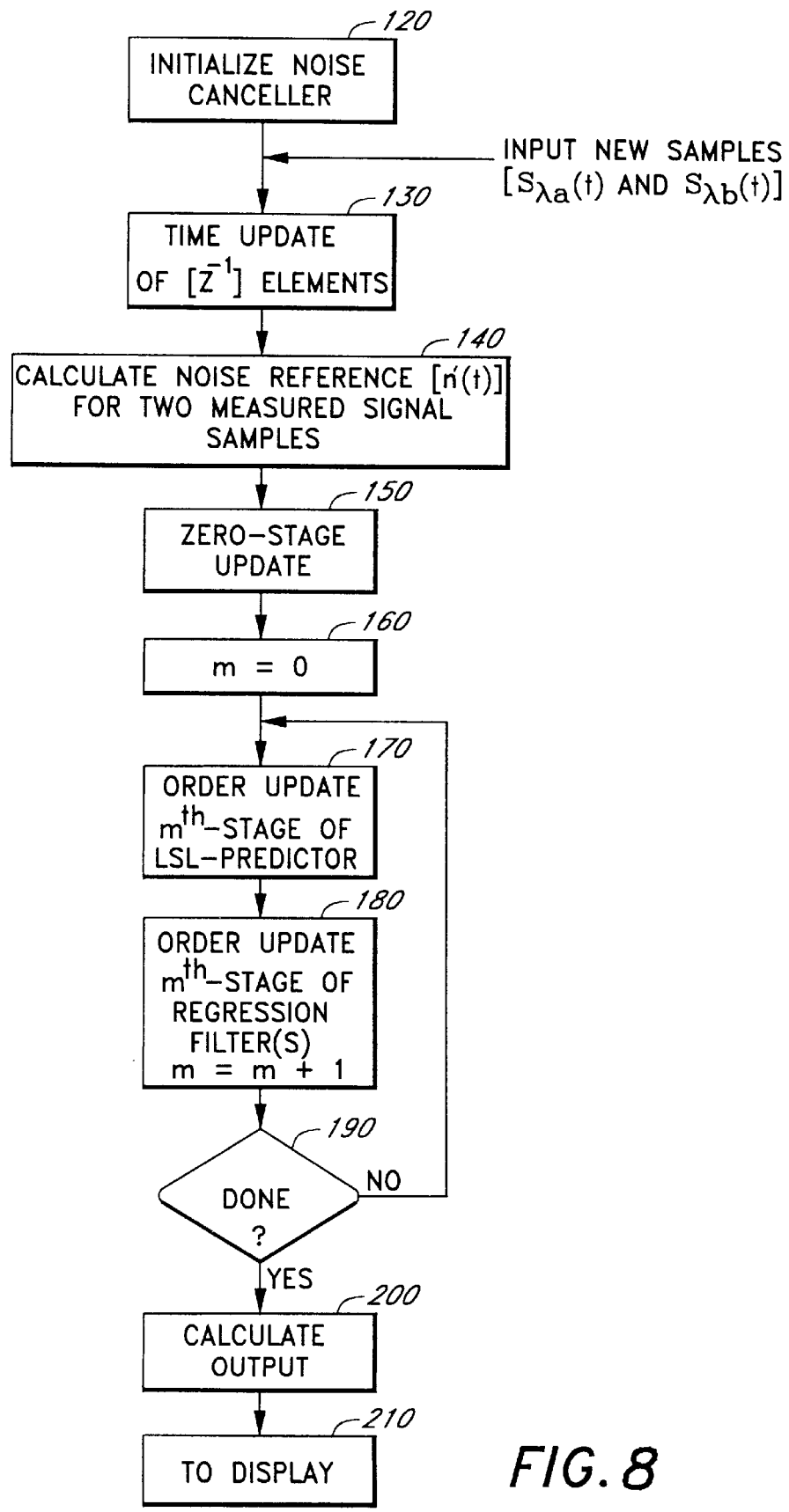
FIG. 8 is a flowchart representing a subroutines capable of implementing a joint process estimator as modeled in FIG. 7.

A flow chart of a subroutine to estimate the desired signal portion $Y_{\lambda a}(t)$ of a sample of a measured signal, $S_{\lambda a}(t)$ is shown in FIG. 8. The flow chart describes how the action of a reference processor for determining the noise reference signal and the joint process estimator 60 would be implemented in software.

A one-time only initialization is performed when the physiological monitor is turned on, as indicated by an "INITIALIZE NOISE CANCELER" box 120. The initialization sets all registers 90, 92, and 96 and delay element variables 110 to the values described above in equations (40) through (44).

Next, a set of simultaneous samples of the measured signals $S_{\lambda a}(t)$ and $S_{\lambda b}(t)$ is input to the subroutine represented by the flowchart in FIG. 8. Then a time update of each of the delay element program variables occurs, as indicated in a "TIME UPDATE OF $[Z^{-1}]$ ELEMENTS" box 130, wherein the value stored in each of the delay element variables 110 is set to the value at the input of the delay element variable 110. Thus, the zero-stage backward prediction error $b_0(t)$ is stored in the first-stage delay element variable, the first-stage backward prediction error $b_1(t)$ is stored in the second-stage delay element variable, and so on.

Then, using the set of measured signal samples $S_{\lambda a}(t)$ and $S_{\lambda b}(t)$, the noise reference signal is calculated according to the ratiometric or the constant saturation method described above. This is indicated by a "CALCULATE NOISE REFERENCE: (n'(t)) FOR TWO MEASURED SIGNAL SAMPLES" box 140. The ratiometric method is generally preferred since no assumptions about constant saturation values need be made.

A zero-stage order update is performed next as indicated in a "ZERO-STAGE UPDATE" box 150. The zero-stage backward prediction error $b_0(t)$, and the zero-stage forward prediction error $f_0(t)$ are set equal to the value of the noise reference signal n'(t). Additionally, the weighted sum of the forward prediction errors $\Im_m(t)$ and the weighted sum of backward prediction errors $\beta_m(t)$ are set equal to the value defined in equation (46).

Next, a loop counter, m, is initialized as indicated in a "m=0" box 160. A maximum value of m, defining the total number of stages to be used by the subroutine corresponding to the flowchart in FIG. 8, is also defined. Typically, the loop is constructed such that it stops iterating once a criterion for convergence upon a best approximation to the desired signal has been met by the joint process estimator 60. Additionally, a maximum number of loop iterations may be chosen at which the loop stops iteration. In a preferred embodiment of a physiological monitor of the present invention, a maximum number of iterations, m=60 to m=80, is advantageously chosen.

Within the loop, the forward and backward reflection coefficient $\Gamma_{f,m}(t)$ and $\Gamma_{b,m}(t)$ register 90 and 92 values in the least-squares lattice filter are calculated first, as indicated by the "ORDER UPDATE MTH CELL OF LSL-LATTICE" box 170 in FIG. 8. This requires calculation of intermediate variable and signal values used in determining register 90, 92, and 96 values in the present stage, the next stage, and in the regression filter 80

The calculation of regression filter register 96 value $\kappa_{m,\lambda a}(t)$ is performed next, indicated by the "ORDER UPDATE MTH STAGE OF REGRESSION FILTER(S)" box 180. The two order update boxes 170 and 180 are performed in sequence m times, until m has reached its predetermined maximum (in the preferred embodiment, m=60 to m=80) or a solution has been converged upon, as indicated by a YES path from a "DONE" decision box 190. In a computer subroutine, convergence is determined by checking if the weighted sums of the forward and backward prediction errors $\Im_m(t)$ and $\beta_m(t)$ are less than a small positive number. An output is calculated next, as indicated by a "CALCULATE OUTPUT" box 200. The output is a good approximation to the desired signal, as determined by the reference processor and joint process estimator 60 subroutine corresponding to the flow chart of FIG. 8. This is displayed (or used in a calculation in another subroutine), as indicated by a "To DISPLAY" box 210.

A new set of samples of the two measured signals $S_{\lambda a}(t)$ and $S_{\lambda b}(t)$ is input to the processor and joint process estimator 60 adaptive noise canceler subroutine corresponding to the flowchart of FIG. 8 and the process reiterates for these samples. Note, however, that the initialization process does not re-occur. New sets of measured signal samples $S_{\lambda a}(t)$ and $S_{\lambda b}(t)$ are continuously input to the reference processor and joint process estimator 60 adaptive noise canceler subroutine. The output forms a chain of samples which is representative of a continuous wave. This waveform is a good approximation to the desired signal waveform $Y'_{\lambda a}(t)$ at wavelength $\lambda a$.

CALCULATION OF SATURATION FROM ADAPTIVE NOISE CANCELER OUTPUT

Physiological monitors typically use the approximation of the desired signal $Y'_{\lambda a}(t)$ to calculate another quantity, such as the saturation of one constituent in a volume containing that constituent plus one or more other constituents. Generally, such calculations require information about a desired signal at two wavelengths. In some measurements, this wavelength is $\lambda b$, the wavelength used in the calculation of the noise reference signal n'(t). For example, the constant saturation method of determining the noise reference signal requires a good approximation of the desired signal portions $Y_{\lambda a}(t)$ and $Y_{\lambda b}(t)$ of both measured signals $S_{\lambda a}(t)$ and $S_{\lambda b}(t)$. Then, the saturation is determined from the approximations to both signals, i.e. $Y'_{\lambda a}(t)$ and $Y'_{\lambda b}(t)$.

In other physiological measurements, information about a signal at a third wavelength is necessary. For example, to find the saturation using the ratiometric method, signals $S_{\lambda a}(t)$ and $S_{\lambda b}(t)$ are used to find the noise reference signal n'(t). But as discussed previously, $\lambda a$ and $\lambda b$ were chosen to satisfy a proportionality relationship like that of equation (22). This proportionality relationship forces the two desired signal portions $Y_{\lambda a}(t)$ and $Y_{\lambda b}(t)$ to be linearly dependent. Generally, linearly dependant mathematical equations cannot be solved for the unknowns. Analogously, some desirable information cannot be derived from two linearly dependent signals. Thus, to determine the saturation using the ratiometric method, a third signal is simultaneously measured at wavelength $\lambda c$. The wavelength $\lambda c$ is chosen such that the desired portion $Y_{\lambda c}(t)$ of the measured signal $S_{\lambda c}(t)$ is not linearly dependent with the desired portions $Y_{\lambda a}(t)$ and $Y_{\lambda b}(t)$ of the measured signals $S_{\lambda a}(t)$ and $S_{\lambda b}(t)$. Since all measurements are taken substantially simultaneously, the noise reference signal n'(t) is correlated to the undesired signal portions $n_{\lambda a}$, $n_{\lambda b}$, and $n_{\lambda c}$ of each of the measured signals $S_{\lambda a}(t)$, $S_{\lambda b}(t)$, and $S_{\lambda c}(t)$ and can be used to estimate approximations to the desired signal portions $Y_{\lambda a}(t)$, $Y_{\lambda b}(t)$, and $Y_{\lambda c}(t)$ for all three measured signals $S_{\lambda a}(t)$, $S_{\lambda b}(t)$, and $S_{\lambda c}(t)$. Using the ratiometric method, estimation of the desired signal portions $Y_{\lambda a}(t)$ and $Y_{\lambda c}(t)$ of two measured signals $S_{\lambda a}(t)$ and $S_{\lambda c}(t)$, chosen, correctly, is usually satisfactory to determine most physiological data.

Figure 9:
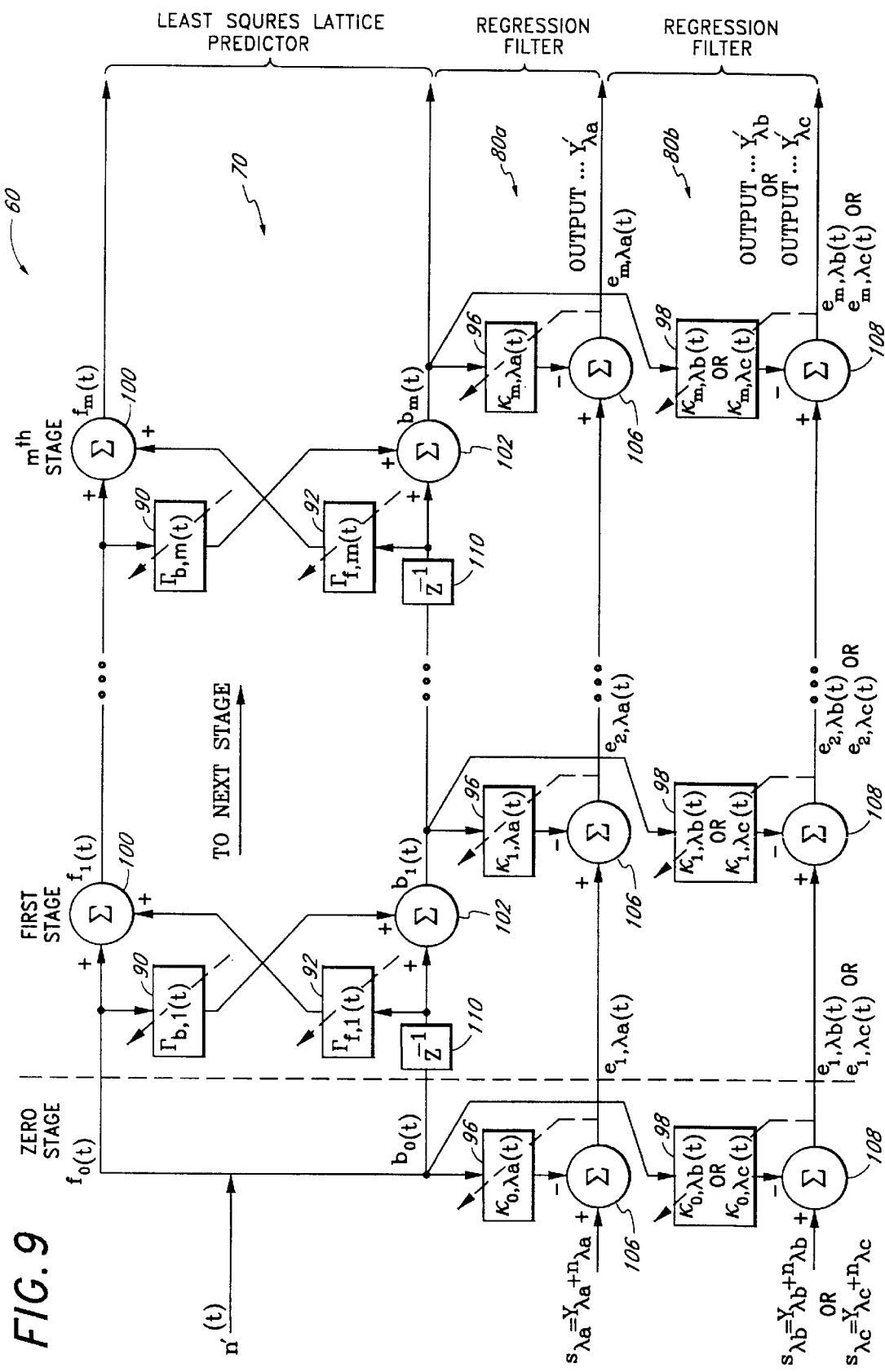
FIG. 9 is a schematic model of a joint process estimator with a least-squares lattice predictor and two regression filters.

A joint process estimator 60 having two regression filters 80a and 80b is shown in FIG. 9. A first regression filter 80a accepts a measured signal $S_{\lambda a}(t)$. A second regression filter 80b accepts a measured signal $S_{\lambda b}(t)$ or $S_{\lambda c}(t)$, depending whether the constant saturation method or the ratiometric method is used to determine the noise reference signal n'(t). The first and second regression filters 80a and 80b are independent. The backward prediction error $b_m(t)$ is input to each regression filter 80a and 80b, the input for the second regression filter 80b bypassing the first regression filter 80a.

The second regression filter 80b comprises registers 98, and summing elements 108 arranged similarly to those in the first regression filter 80a. The second regression filter 80b operates via an additional intermediate variable in conjunction with those defined by equations (48) through (58), i.e.:

$$\rho_{m,\lambda b}(t)=\lambda\rho_{m,\lambda b}(t-1)+\{b_m(t)e^*_{m,\lambda b}(t)/\gamma_m(t)\}; \text{ or} \quad (59)$$

$$\rho_{m,\lambda c}(t)=\lambda\rho_{m,\lambda c}(t-1)+\{b_m(t)e^*_{m,\lambda c}(t)/\gamma_m(t)\}; \text{ and} \quad (60)$$

$$\rho_{0,\lambda b}(0)=0; \text{ or} \quad (61)$$

$$\rho_{0,\lambda c}(0)=0. \quad (62)$$

The second regression filter 80b has an error signal value defined similar to the first regression filter error signal values, $e_{m+1,\lambda a}(t)$, i.e.:

$$e_{m+1,\lambda b}(t)=e_{m,\lambda b}(t)-\kappa^*_{m,\lambda b}(t)b_m(t); \text{ or} \quad (63)$$

$$e_{m+1,\lambda c}(t)=e_{m,\lambda c}(t)-\kappa^*_{m,\lambda b}(t)b_m(t); \text{ and} \quad (64)$$

$$e_{0,\lambda b}(t)=S_{\lambda b}(t) \text{ for } t\geq 0; \text{ or} \quad (65)$$

$$e_{0,\lambda c}(t)=S_{\lambda c}(t) \text{ for } t\geq 0. \quad (66)$$

The second regression filter has a regression coefficients $\kappa_{m,\lambda b}(t)$ register 98 value defined similarly to the first regression filter error signal values, i.e.:

$$\kappa_{m,\lambda b}(t)=\{\rho_{m,\lambda b}(t)/\beta_m(t)\}; \text{ or} \quad (67)$$

$$\kappa_{m,\lambda c}(t)=\{\rho_{m,\lambda c}(t)/\beta_m(t)\}; \quad (68)$$

These values are used in conjunction with those intermediate variable values, signal values, register and register values defined in equations (40) through (58). These signals are calculated in an order defined by placing the additional signals immediately adjacent a similar signal for the wavelength $\lambda a$.

For the ratiometric method, $S_{\lambda c}(t)$ is input to the second regression filter 80b. The output of the second regression filter 80b is then a good approximation to the desired signal $Y'_{\lambda c}(t)$. For the constant saturation method, $S_{\lambda b}(t)$ is input to the second regression filter 80b. The output is then a good approximation to the desired signal $Y'_{\lambda b}(t)$.

The addition of the second regression filter 80b does not substantially change the computer program subroutine represented by the flowchart of FIG. 8. Instead of an order update of the $m^{th}$ stage of only one regression filter, an order update of the $m^{th}$ stage of both regression filters 80a and 80b is performed. This is characterized by the plural designation in the "ORDER UPDATE OF $m^{th}$ STAGE OF REGRESSION FILTER(S)" box 180 in FIG. 8. Since the regression filters 80a and 80b operate independently, independent calculations can be performed in the reference processor and joint process estimator 60 adaptive noise canceler subroutine modeled by the flowchart of FIG. 8.

CALCULATION OF SATURATION

Once good approximations to the desired signals, $Y'_{\lambda a}(t)$ and $Y'_{\lambda c}(t)$ for the ratiometric method and $Y'_{\lambda a}(t)$ and $Y'_{\lambda b}(t)$ for the constant saturation method, have been determined by the joint process estimator 60, the saturation of $A_5$ in a volume containing $A_5$ and $A_6$, for example, may be calculated according to various known methods. Mathematically, the approximations to the desired signals can be written:

$$Y'_{\lambda a}(t) \approx \epsilon_{5,\lambda a} c_5 x_{5,6}(t) + \epsilon_{6,\lambda a} c_6 x_{5,6}(t); \text{ and} \quad (69)$$

$$Y'_{\lambda c}(t) \approx \epsilon_{5,\lambda c} c_5 x_{5,6}(t) + \epsilon_{6,\lambda c} c_6 x_{5,6}(t); \quad (70)$$

for the ratiometric method using wavelengths $\lambda a$ and $\lambda c$. For the constant saturation method, the approximations to the desired signals can be written in terms of $\lambda a$ and $\lambda b$ as:

$$Y'_{\lambda a}(t) \approx \epsilon_{5,\lambda a} c_5 x_{5,6}(t) + \epsilon_{6,\lambda a} c_6 x_{5,6}(t); \text{ and} \quad (71)$$

$$Y'_{\lambda b}(t) \approx \epsilon_{5,\lambda b} c_5 x_{5,6}(t) + \epsilon_{6,\lambda b} c_6 x_{5,6}(t). \quad (72)$$

This is equivalent to two equations having three unknowns, namely $c_5(t)$, $c_6(t)$ and $X_{5,6}(t)$. In both the ratiometric and the constant saturation cases, the saturation can be determined by acquiring approximations to the desired signal portions at two different, yet proximate times $t_1$ and $t_2$ over which the saturation of $A_5$ in the volume containing $A_5$ and $A_6$ does not change substantially. For example, for the desired signals estimated by the ratiometric method, at times $t_1$ and $t_2$:

$$Y'_{\lambda a}(t_1) \approx \epsilon_{5,\lambda a} c_5 x_{5,6}(t_1) + \epsilon_{6,\lambda a} c_6 x_{5,6}(t_1) \quad (73)$$

$$Y'_{\lambda c}(t_1) \approx \epsilon_{5,\lambda c} c_5 x_{5,6}(t_1) + \epsilon_{6,\lambda c} c_6 x_{5,6}(t_1) \quad (74)$$

$$Y'_{\lambda a}(t_2) \approx \epsilon_{5,\lambda a} c_5 x_{5,6}(t_2) + \epsilon_{6,\lambda a} c_6 x_{5,6}(t_2) \quad (75)$$

$$Y'_{\lambda c}(t_2) \approx \epsilon_{5,\lambda c} c_5 x_{5,6}(t_2) + \epsilon_{6,\lambda c} c_6 x_{5,6}(t_2) \quad (76)$$

Then, difference signals may be determined which relate the signals of equation (73) through (76), i.e.:

$$\Delta Y_{\lambda a} = Y'_{\lambda a}(t_1) - Y'_{\lambda a}(t_2) \approx \epsilon_{5,\lambda a} c_5 \Delta x + \epsilon_{6,\lambda a} c_6 \Delta x; \text{ and} \quad (77)$$

$$\Delta Y_{\lambda c} = Y'_{\lambda c}(t_1) - Y'_{\lambda c}(t_2) \approx \epsilon_{5,\lambda c} c_5 \Delta x + \epsilon_{6,\lambda c} c_6 \Delta x; \quad (78)$$

where $\Delta x = x_{5,6}(t_1) - x_{5,6}(t_2)$. The average saturation at time $t = (t_1 + t_2)/2$ is:

$$\text{Saturation}(t) = c_5(t)/[c_5(t) + c_6(t)] \quad (79)$$

$$= \frac{\epsilon_{6,\lambda a} - \epsilon_{6,\lambda b}\left(\frac{\Delta Y_{\lambda a}}{\Delta Y_{\lambda b}}\right)}{\epsilon_{6,\lambda a} - \epsilon_{5,\lambda a} - (\epsilon_{6,\lambda b} - \epsilon_{5,\lambda b})\left(\frac{\Delta Y_{\lambda a}}{\Delta Y_{\lambda b}}\right)} \quad (80)$$

It will be understood that the $\Delta x$ term drops out from the saturation calculation because of the division. Thus, knowledge of the thickness of the desired constituents is not required to calculate saturation.

PULSE OXIMETRY MEASUREMENTS

A specific example of a physiological monitor utilizing a processor of the present invention to determine a noise reference signal $n'(t)$ for input to an adaptive noise canceler that removes erratic motion-induced undesired signal portions is a pulse oximeter. A pulse oximeter typically causes energy to propagate through a medium where blood flows close to the surface for example, an ear lobe, or a digit such as a finger, or a forehead. An attenuated signal is measured after propagation through or reflection from the medium. The pulse oximeter estimates the saturation of oxygenated blood available to the body for use.

Freshly oxygenated blood is pumped at high pressure from the heart into the arteries for use by the body. The volume of blood in the arteries varies with the heartbeat, giving rise to a variation in absorption of energy at the rate of the heartbeat, or the pulse.

Oxygen depleted, or deoxygenated, blood is returned to the heart by the veins along with unused oxygenated blood. The volume of blood in the veins varies with the rate of breathing, which is typically much slower than the heartbeat. Thus, when there is no motion induced variation in the thickness of the veins, venous blood causes a low frequency variation in absorption of energy. When there is motion induced variation in the thickness of the veins, the low frequency variation in absorption is coupled with the erratic variation in absorption due to motion artifact.

In absorption measurements using the transmission of energy through a medium, two light emitting diodes (LED's) are positioned on one side of a portion of the body where blood flows close to the surface, such as a finger, and a photodetector is positioned on the opposite side of the finger. Typically, in pulse oximetry measurements, one LED emits a visible wavelength, preferably red, and the other LED emits an infrared wavelength. However, one-skilled in the art will realize that other wavelength combinations could be used.

The finger comprises skin, tissue, muscle, both arterial blood and venous blood, fat, etc., each of which absorbs light energy differently due to different absorption coefficients, different concentrations, and different thicknesses. When the patient is not moving, absorption is substantially constant except for the flow of blood. This constant attenuation can be determined and subtracted from the signal via traditional filtering techniques. When the patient moves, the absorption becomes erratic. Erratic motion induced noise typically cannot be predetermined and subtracted from the measured signal via traditional filtering techniques. Thus, determining the saturation of oxygenated arterial blood becomes more difficult.

Figure 10:
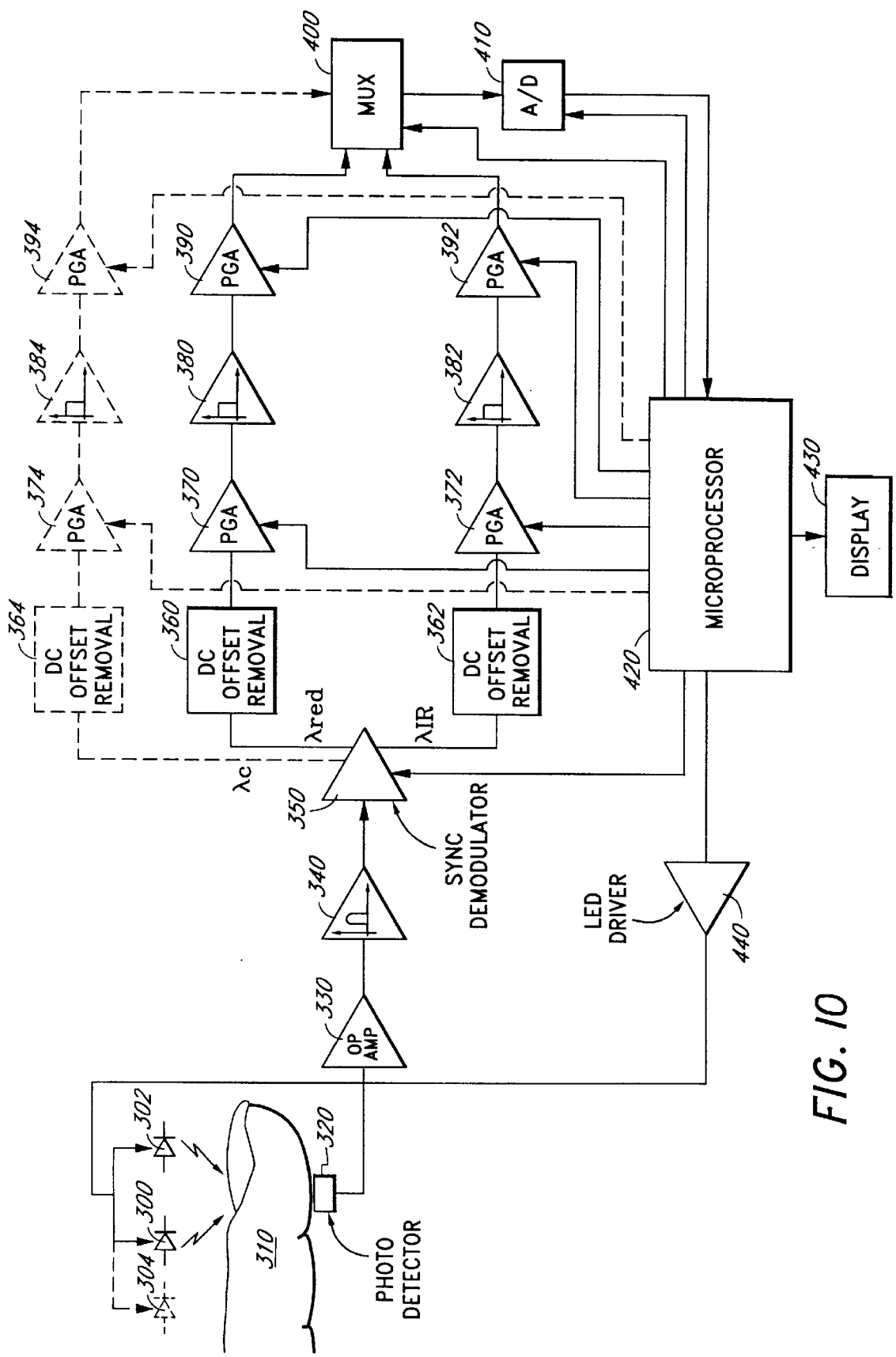
FIG. 10 is an example of a physiological monitor incorporating a processor of the present invention and an adaptive noise canceler within a microprocessor. This physiological monitor is specifically designed to measure a plethysmographic waveform and perform pulse oximetry measurements.

A schematic of a physiological monitor for pulse oximetry is shown in FIG. 10. Two LED's 300 and 302, one LED 300 emitting red wavelengths and another LED 302 emitting infrared wavelengths, are placed adjacent a finger 310. A photodetector 320, which produces an electrical signal corresponding to the attenuated visible and infrared light energy signals is located opposite the LED's 300 and 302. The photodetector 320 is connected to a single channel of common processing circuitry including an amplifier 330 which is in turn connected to a band pass filter 340. The band pass filter 340 passes signal into a synchronized demodulator 350 which has a plurality of output channels. One output channel is for signals corresponding to visible wavelengths and another output channel is for signals corresponding to infrared wavelengths.

The output channels of the synchronized demodulator for signals corresponding to both the visible and infrared wavelengths are each connected to separate paths, each path comprising further processing circuitry. Each path includes a DC offset removal element 360 and 362, such as a differential amplifier, a programmable gain amplifier 370 and 372 and a low pass filter 380 and 382. The output of each low pass filter 380 and 382 is amplified in a second programmable gain amplifier 390 and 392 and then input to a multiplexer 400.

The multiplexer 400 is connected to an analog-to-digital converter 410 which is in turn connected to a microprocessor 420. Control lines between the microprocessor 420 and the multiplexer 400, the microprocessor 420 and the analog-to-digital converter 410, and the microprocessor 420 and each programmable gain amplifier 370, 372, 390, and 392 are formed. The microprocessor 420 has additional control lines, one of which leads to a display 430 and the other of which leads to an LED driver 440 situated in a feedback loop with the two LED's 300 and 302.

The LED's 300 and 302 each emits energy which is absorbed by the finger 310 and received by the photodetector 320. The photodetector 320 produces an electrical signal which corresponds to the intensity of the light energy striking the photodetector 320 surface. The amplifier 330 amplifies this electrical signal for ease of processing. The band pass filter 340 then removes unwanted high and low frequencies. The synchronized demodulator 350 separates the electrical signal into electrical signals corresponding to the red and infrared light energy components. A predetermined reference voltage, $V_{ref}$, is subtracted by the DC offset removal element 360 and 362 from each of the separate signals to remove substantially constant absorption which corresponds to absorption when there is no motion induced undesired signal component. Then the first programmable gain amplifiers 370 and 372 amplify each signal for ease of manipulation. The low pass filters 380 and 382 integrate each signal to remove unwanted high frequency components and the second programmable gain amplifiers 390 and 392 amplify each signal for further ease of processing.

The multiplexer 400 acts as an analog switch between the electrical signals corresponding to the red and the infrared light energy, allowing first a signal corresponding to the red light to enter the analog-to-digital convertor 410 and then a signal corresponding to the infrared light to enter the analog-to-digital convertor 410. This eliminates the need for multiple analog-to-digital convertors 410. The analog-to-digital convertor 410 inputs the data into the microprocessor 420 for calculation of a noise reference signal via the processing technique of the present invention and removal of undesired signal portions via an adaptive noise canceler. The microprocessor 420 centrally controls the multiplexer 400, the analog-to-digital convertor 410, and the first and second programmable gain amplifiers 370 and 390 for both the red and the infrared channels. Additionally, the microprocessor 420 controls the intensity of the LED's 302 and 304 through the LED driver 440 in a servo loop to keep the average intensity received at the photodetector 320 within an appropriate range. Within the microprocessor 420 a noise reference signal n'(t) is calculated via either the constant saturation method or the ratiometric method, as described above, the ratiometric method being generally preferred. This signal is used in an adaptive noise canceler of the joint process estimator type 60, described above.

The multiplexer 400 time multiplexes, or sequentially switches between, the electrical signals corresponding to the red and the infrared light energy. This allows a single channel to be used to detect and begin processing the electrical signals. For example, the red LED 300 is energized first and the attenuated signal is measured at the photodetector 320. An electrical signal corresponding to the intensity of the attenuated red light energy is passed to the common processing circuitry. The infrared LED 302 is energized next and the attenuated signal is measured at the photodetector 320. An electrical signal corresponding to the intensity of the attenuated infrared light energy is passed to the common processing circuitry. Then, the red LED 300 is energized again and the corresponding electrical signal is passed to the common processing circuitry. The sequential energization of LED's 300 and 302 occurs continuously while the pulse oximeter is operating.

The processing circuitry is divided into distinct paths after the synchronized demodulator 350 to ease time constraints generated by time multiplexing. In the preferred embodiment of the pulse oximeter shown in FIG. 10, a sample rate, or LED energization rate, of 1000 Hz is advantageously employed. Thus, electrical signals reach the synchronized demodulator 350 at a rate of 1000 Hz. Time multiplexing is not used in place of the separate paths due to settling time constraints of the low pass filters 380, 382, and 384.

In FIG. 10, a third LED 304 is shown adjacent the finger, located near the LED's 300 and 302. The third LED 304 is used to measure a third signal $S_{\lambda c}(t)$ to be used to determine saturation using the ratiometric method. The third LED 304 is time multiplexed with the red and infrared LED's 300 and 302. Thus, a third signal is input to the common processing circuitry in sequence with the signals from the red and infrared LED's 300 and 302. After passing through and being processed by the operational amplifier 330, the band pass filter 340, and the synchronized demodulator 350, the third electrical signal corresponding to light energy at wavelength λc is input to a separate path including a DC offset removal element 364, a first programmable gain amplifier 374, a low pass filter 384, and a second programmable gain amplifier 394. The third signal is then input to the multiplexer 400.

The dashed line connection for the third LED 304 indicates that this third LED 304 is incorporated into the pulse oximeter when the ratiometric method is used; it is unnecessary for the constant saturation method. When the third LED 304 is used, the multiplexer 400 acts as an analog switch between all three LED 300, 302, and 304 signals. If the third LED 304 is utilized, feedback loops between the microprocessor 420 and the first and second programmable gain amplifier 374 and 394 in the λc wavelength path are also formed.

For pulse oximetry measurements using the ratiometric method, the signals (logarithm converted) transmitted through the finger 310 at each wavelength $\lambda a$, $\lambda b$, and $\lambda c$ are:

$$S_{\lambda a}(t)=S_{\lambda,red1}(t)=\epsilon_{Hb02,\lambda a}C_{Hb02}{}^{A}X^{A}(t)+\epsilon_{Hb,\lambda a}C_{Hb}{}^{A}X^{A}(t)+\epsilon_{Hb02,\lambda a}C_{Hb02}{}^{V}X^{V}(t)+\epsilon_{Hb,\lambda a}C_{Hb}{}^{V}X^{V}(t)+n_{\lambda a}(t). \quad (81)$$

$$S_{\lambda b}(t)=S_{\lambda,red2}(t)=\epsilon_{Hb02,\lambda b}C_{Hb02}{}^{A}X^{A}(t)+\epsilon_{Hb,\lambda b}C_{Hb}{}^{A}X^{A}(t)+\epsilon_{Hb02,\lambda b}C_{Hb02}{}^{V}X^{V}(t)+\epsilon_{Hb,\lambda b}C_{Hb}{}^{V}X^{V}(t)+n_{\lambda b}(t). \quad (82)$$

$$S_{\lambda c}(t)=S_{\lambda,IR}(t)=\epsilon_{Hb02,\lambda c}C_{Hb02}{}^{A}X^{A}(t)+\epsilon_{Hb,\lambda c}C_{Hb}{}^{A}X^{A}(t)+\epsilon_{Hb02,\lambda c}C_{Hb02}{}^{V}X^{V}(t)+\epsilon_{Hb,\lambda c}C_{Hb}{}^{V}X^{V}+n_{\lambda c}(t). \quad (83)$$

In equations (81) through (83), $X^{A}(t)$ is the lump-sum thickness of the arterial blood in the finger; $X^{V}(t)$ is the lump-sum thickness of venous blood in the finger; $\epsilon_{Hb02,\lambda a}$, $\epsilon_{Hb02,\lambda b}$, $\epsilon_{Hb02,\lambda c}$, $\epsilon_{Hb,\lambda a}$, $\epsilon_{Hb,\lambda b}$, and $\epsilon_{Hb,\lambda c}$ are the absorption coefficients of the oxygenated and non-oxygenated hemoglobin, at each wavelength measured; and $c_{Hb02}(t)$ and $c_{Hb}(t)$ with the superscript designations A and V are the concentrations of the oxygenated and non-oxygenated arterial blood and venous blood, respectively.

For the ratiometric method, the wavelengths chosen are typically two in the visible red range, i.e., $\lambda a$ and $\lambda b$, and one in the infrared range, i.e., $\lambda c$. As described above, the measurement wavelengths $\lambda a$ and $\lambda b$ are advantageously chosen to satisfy a proportionality relationship which removes the desired signal portion $Y_{\lambda a}(t)$ and $Y_{\lambda b}(t)$, yielding a noise reference signal n'(t). In the preferred embodiment, the ratiometric method is used to determine the noise reference signal n'(t) by picking two wavelengths that cause the desired portions $Y_{\lambda a}(t)$ and $Y_{\lambda b}(t)$ of the measured signals $S_{\lambda a}(t)$ and $S_{\lambda b}(t)$ to become linearly dependent similarly to equation (22): i.e. wavelengths $\lambda a$ and $\lambda b$ which satisfy:

$$\epsilon_{Hb02,\lambda a}/\epsilon_{Hb,\lambda a}=\epsilon_{Hb02,\lambda b}/\epsilon_{Hb,\lambda b} \quad (84)$$

Typical wavelength values chosen are $\lambda a$ 650 nm and $\lambda b$=685 nm. Additionally a typical wavelength value for $\lambda c$ is $\lambda c$=940 nm. By picking wavelengths $\lambda a$ and $\lambda b$ to satisfy equation (84) the venous portion of the measured signal is also caused to become linearly dependent even though it is not a portion of the desired signal. Thus, the venous portion of the signal is removed with the desired portion. The proportionality relationship between equations (81) and (82) which allows determination of a non-zero noise reference signal n'(t), similarly to equation (25) is:

$$\omega_{r4}=\epsilon_{Hb,\lambda a}/\epsilon_{Hb,\lambda b}; \text{ where} \quad (85)$$

$$n_{\lambda a}(t)\neq\omega_{r4}n_{\lambda b}(t). \quad (86)$$

In pulse oximetry, both equations (85) and (86) can typically be satisfied simultaneously.

Figure 11:
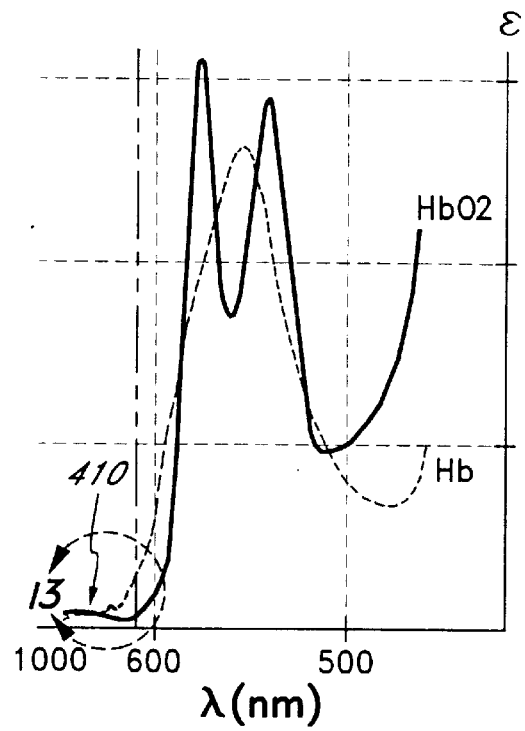
FIG. 11 is a graph of oxygenated and deoxygenated absorption coefficients vs. wavelength.
Figure 13:
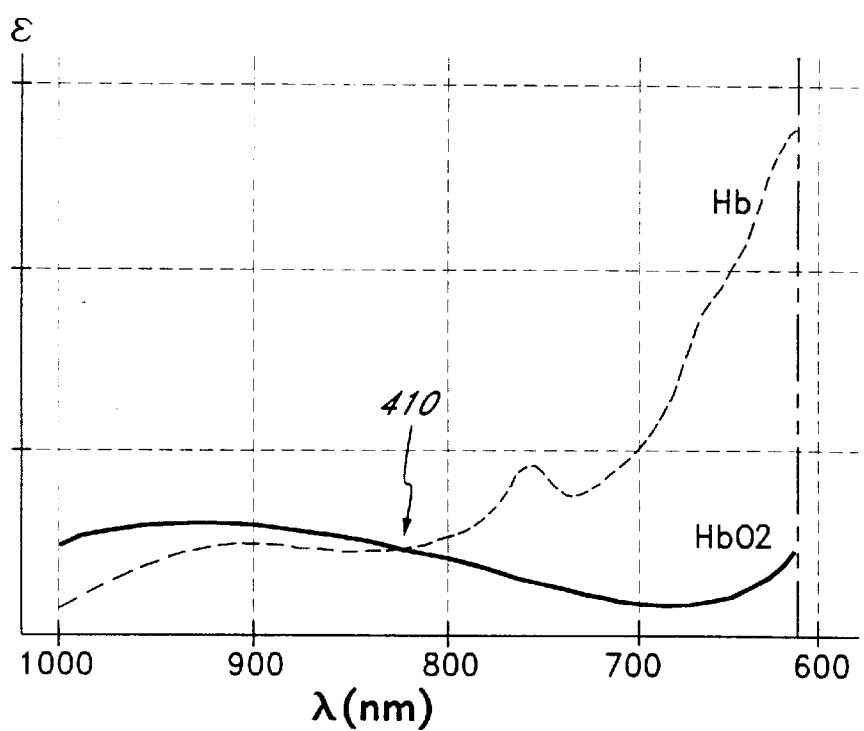
FIG. 13 is an expanded view of a portion of FIG. 11 marked by a circle labelled 13.
Figure 12:
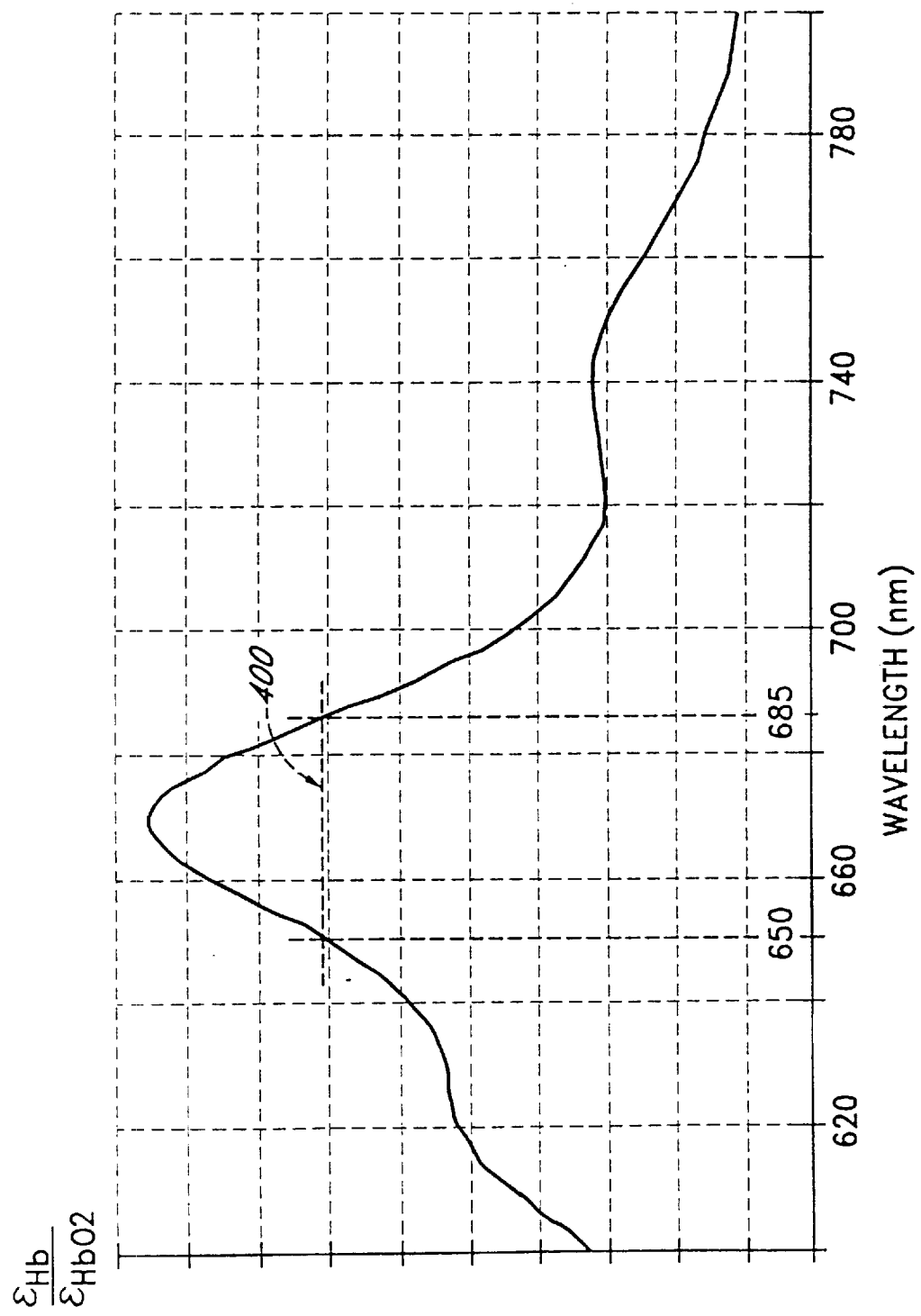
FIG. 12 is a graph of the ratio of the absorption coefficients of deoxygenated hemoglobin divided by oxygenated hemoglobin vs. wavelength.

FIG. 11 is a graph of the absorption coefficients of oxygenated and deoxygenated hemoglobin ($\epsilon_{Hb02}$ and $\epsilon_{Hb}$) vs. wavelength ($\lambda$). FIG. 12 is a graph of the ratio of absorption coefficients vs. wavelength, i.e., $\epsilon_{Hb}/\epsilon_{Hb02}$ vs. $\lambda$ over the range of wavelength within circle 13 in FIG. 11. Anywhere a horizontal line touches the curve of FIG. 12 twice, as does line 400, the condition of equation (84) is satisfied. FIG. 13 shows an exploded view of the area of FIG. 11 within the circle 13. Values of $\epsilon_{Hb02}$ and $\epsilon_{Hb}$ at the wavelengths where a horizontal line touches the curve of FIG. 12 twice can then be determined from the data in FIG. 13 to solve for the proportionality relationship of equation (85).

A special case of the ratiometric method is when the absorption coefficients $\epsilon_{Hb02}$ and $\epsilon_{Hb}$ are equal at a wavelength. Arrow 410 in FIG. 11 indicates one such location, called an isobestic point. FIG. 13 shows an exploded view of the isobestic point. To use isobestic points with the ratiometric method, two wavelengths at isobestic points are determined to satisfy equation (84).

Multiplying equation (82) by $\omega_{r4}$ and then subtracting equation (82) from equation (81), a non-zero noise reference signal n'(t) is determined by:

$$n'(t)=S_{\lambda a}(t)-\omega_{r4}S_{\lambda b}(t)=n_{\lambda a}(t)-\omega_{r4}n_{\lambda b}. \quad (87)$$

This noise reference signal n'(t) has spectral content corresponding to the erratic, motion-induced noise. When it is input to an adaptive noise canceler, with either the signals $S_{\lambda a}(t)$ and $S_{\lambda c}(t)$ or $S_{\lambda b}(t)$ and $S_{\lambda c}(t)$ input to two regression filters 80a and 80b, the adaptive noise canceler will function much like an adaptive multiple notch filter and remove frequency components present in both the noise reference signal n'(t) and the measured signals from the measured signals $S_{\lambda a}(t)$ and $S_{\lambda c}(t)$ or $S_{\lambda b}(t)$ and $S_{\lambda c}(t)$. Thus, the adaptive noise canceler is able to remove erratic noise caused in the venous portion of the measured signals $S_{\lambda a}(t)$, $S_{\lambda b}(t)$, and $S_{\lambda c}(t)$ even though the venous portion of the measured signals $S_{\lambda a}(t)$ and $S_{\lambda b}(t)$ was not incorporated in the noise reference signal n'(t). However, the low frequency absorption caused by venous blood moving through the veins is generally not one of the frequencies incorporated into the noise reference signal n'(t). Thus, the adaptive noise canceler generally will not remove this portion of the undesired signal. However, a band pass filter applied to the approximations to the desired signals $Y'_{\lambda a}(t)$ and $Y'_{\lambda c}(t)$ or $Y'_{\lambda b}(t)$ and $Y'_{\lambda c}(t)$ can remove this portion of the undesired signal corresponding to the low frequency venous absorption.

For pulse oximetry measurements using the constant saturation method, the signals (logarithm converted) transmitted through the finger 310 at each wavelength $\lambda a$ and $\lambda b$ are:

$$S_{\lambda a}(t)=S_{\lambda,red1}(t)=\epsilon_{Hb02,\lambda a}C_{Hb02}{}^{A}X^{A}(t)+\epsilon_{Hb,\lambda a}C_{Hb}{}^{A}X^{A}(t)+\epsilon_{Hb02,\lambda a}C_{Hb02}{}^{V}X^{V}(t)+\epsilon_{Hb,\lambda a}C_{Hb}{}^{V}X^{V}(t)+n_{\lambda a}(t). \quad (88)$$

$$S_{\lambda b}(t)=S_{\lambda,IR}(t)=\epsilon_{Hb02,\lambda b}C_{Hb02}{}^{A}X^{A}(t)+\epsilon_{Hb,\lambda b}C_{Hb}{}^{A}X^{A}(t)+\epsilon_{Hb02,\lambda b}C_{Hb02}{}^{V}X^{V}(t)+\epsilon_{Hb,\lambda b}C_{Hb}{}^{V}X^{V}(t)+n_{\lambda b}(t). \quad (89)$$

For the constant saturation method, the wavelengths chosen are typically one in the visible red range, i.e., $\lambda a$, and one in the infrared range, i.e., $\lambda b$. Typical wavelength values chosen are $\lambda a$=660 nm and $\lambda b$=940 nm. Using the constant saturation method, it is assumed that $C_{Hb02}(t)/C_{Hb}(t)$= constant. The saturation of oxygenated arterial blood changes slowly, if at all, with respect to the sample rate, making this a valid assumption. The proportionality factor between equation (88) and (89) can then be written as:

$$\omega_{s4}(t)=\frac{\epsilon_{Hb02,\lambda a}C_{Hb02}x(t)+\epsilon_{Hb,\lambda a}C_{Hb}x(t)}{\epsilon_{Hb02,\lambda b}C_{Hb02}x(t)+\epsilon_{Hb,\lambda b}C_{Hb}x(t)} \quad (90)$$

$$\approx Y'_{\lambda a}(t)/Y'_{\lambda b}(t); \text{ where} \quad (91)$$

$$n_{\lambda a}(t)\neq\omega_{a4}(t)n_{\lambda b}(t). \quad (92)$$

In pulse oximetry, it is typically the case that both equations (91) and (92) can be satisfied simultaneously.

Multiplying equation (89) by $\omega_{a4}(t)$ and then subtracting equation (89) from equation (88), a non-zero noise reference signal n'(t) is determined by:

$$n'(t) = S_{\lambda a}(t) - \omega_{a4}(t) S_{\lambda b}(t) \quad (93)$$

$$= \epsilon_{Hbo2,\lambda a} C_{Hbo2}{}^V X^V(t) + \epsilon_{Hb,\lambda a} C_{Hb}{}^V X^V(t) + n_{\lambda a}(t) - \omega_{a4}[\epsilon_{Hbo2,\lambda b} C_{Hbo2}{}^V X^V(t) + \epsilon_{Hb,\lambda b} C_{Hb}{}^V X^V(t) + n_{\lambda b}(t)]. \quad (94)$$

The constant saturation assumption does not cause the venous contribution to the absorption to be canceled along with the desired signal portions $Y_{\lambda a}(t)$ and $Y_{\lambda b}(t)$, as did the relationship of equation (84) used in the ratiometric method. Thus, frequencies associated with both the low frequency modulated absorption due to venous absorption when the patient is still and the erratically modulated absorption due to venous absorption when the patient is moving are represented in the noise reference signal n'(t). Thus, the adaptive canceler can remove both erratically modulated absorption due to venous blood in the finger under motion and the constant low frequency cyclic absorption of venous blood.

Using either method, a noise reference signal n'(t) is determined by the processor of the present invention for use in an adaptive noise canceler which is defined by software in the microprocessor. The preferred adaptive noise canceler is the joint process estimator 60 described above.

Figure 14:
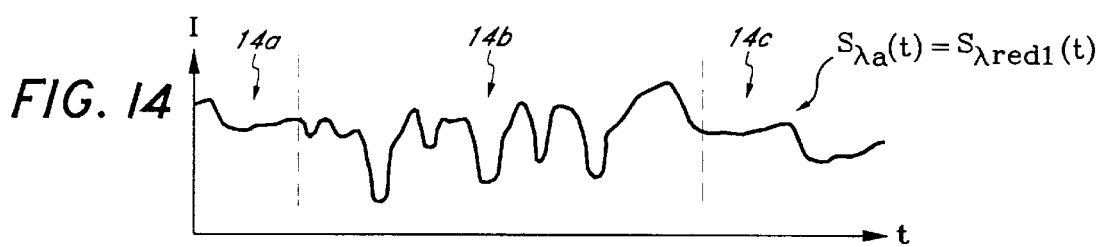
FIG. 14 illustrates a signal measured at a first red wavelength $\lambda a=\lambda red1=650$ nm for use in a processor of the present invention employing the ratiometric method for determining the noise reference signal n'(t) and for use in a joint process estimator. The measured signal comprises a desired portion $_{\lambda a}(t)$ and an undesired portion $n_{\lambda a}(t)$.
Figure 15:
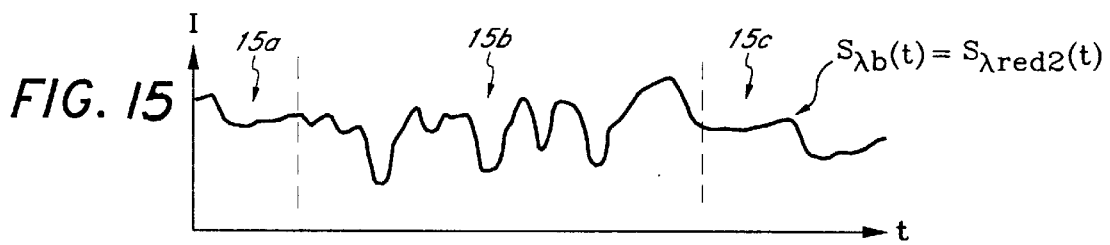
FIG. 15 illustrates a signal measured at a second red wavelength $\lambda b=\lambda red2=685$ nm for use in a processor of the present invention employing the ratiometric method for determining the noise reference signal n'(t). The measured signal comprises a desired portion $Y_{\lambda b}(t)$ and an undesired portion $n_{\lambda b}(t)$.
Figure 16:
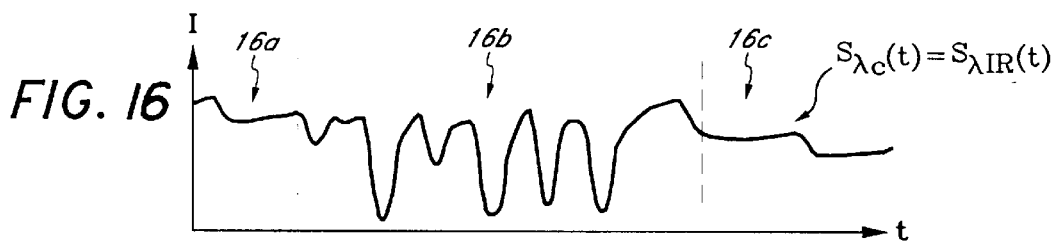
FIG. 16 illustrates a signal measured at an infrared wavelength $\lambda c=\lambda IR=940$ nm for use in a joint process estimator. The measured signal comprises a desired portion $Y_{\lambda c}(t)$ and an undesired portion $n_{\lambda c}(t)$.

Illustrating the operation of the ratiometric method of the present invention, FIGS. 14, 15 and 16 show signals measured for use in determining the saturation of oxygenated arterial blood using a reference processor of the present invention which employs the ratiometric method, i.e., the signals $S_{\lambda a}(t) = S_{\lambda red1}(t)$, $S_{\lambda b}(t) = S_{\lambda red2}(t)$, and $S_{\lambda c}(t) = S_{\lambda IR}(t)$. A first segment 14a, 15a, and 16a of each of the signals is relatively undisturbed by motion artifact, i.e., the patient did not move substantially during the time period in which these segments were measured. These segments 14a, 15a, and 16a are thus generally representative of the desired plethysmographic waveform at each of the measured wavelengths. A second segment 14b, 15b, and 16b of each of the signals is affected by motion artifact, i.e., the patient did move during the time period in which these segments were measured. Each of these segments 14b, 15b, and 16b shows large motion induced excursions in the measured signal. A third segment 14c, 15c, and 16c of each of the signals is again relatively unaffected by motion artifact and is thus generally representative of the desired plethysmographic waveform at each of the measured wavelengths.

Figure 17:
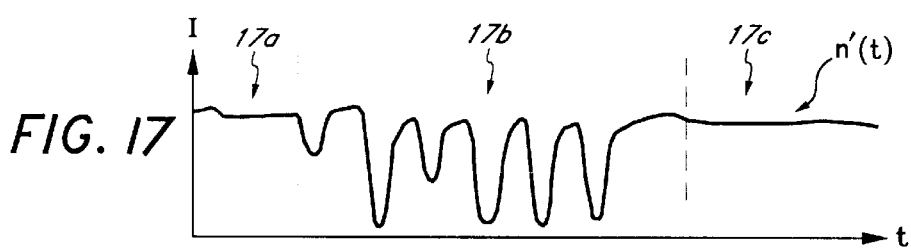
FIG. 17 illustrates the noise reference signal n'(t) determined by a processor of the present invention using the ratiometric method.

FIG. 17 shows the noise reference signal n'(t)=$n_{\lambda a}$-$\omega_r n_{\lambda b}(t)$, as determined by a reference processor of the present invention utilizing the ratiometric method. As discussed previously, the noise reference signal n'(t) is correlated to the undesired signal portions $n_{\lambda a}$, $n_{\lambda b}$, and $n_{\lambda c}$. Thus, a first segment 17a of the noise reference signal n'(t) is generally flat, corresponding to the fact that there is very little motion induced noise in the first segments 14a, 15a, and 16a of each signal. A second segment 17b of the noise reference signal n'(t) exhibits large excursions, corresponding to the large motion induced excursions in each of the measured signals. A third segment 17c of the noise reference signal n'(t) is generally flat, again corresponding to the lack of motion artifact in the third segments 14a, 14b, and 14c of each measured signal.

Figure 18:
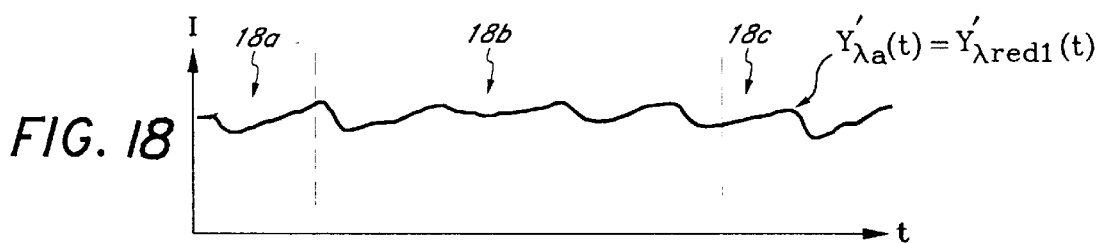
FIG. 18 illustrates a good approximation $Y'_{\lambda a}(t)$ to the desired portion $Y_{\lambda a}(t)$ of the signal $S_{\lambda a}(t)$ measured at $\lambda a=\lambda red1=650$ nm estimated with a noise reference signal n'(t) determined by the ratiometric method.
Figure 19:
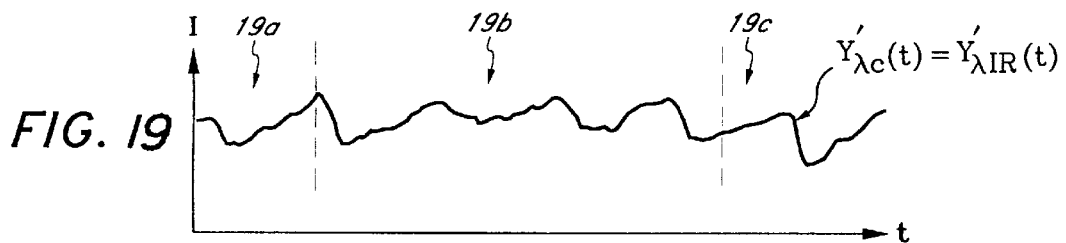
FIG. 19 illustrates a good approximation $Y'_{\lambda c}(t)$ to the desired portion $Y_{\lambda c}(t)$ of the signal $S_{\lambda c}(t)$ measured at $\lambda c=\lambda IR=940$ nm estimated with a noise reference signal n'(t) determined by the ratiometric method.

FIGS. 18 and 19 show the approximations $Y'_{\lambda a}(t)$ and $Y'_{\lambda c}(t)$ to the desired signals $Y_{\lambda a}(t)$ and $Y_{\lambda c}(t)$ as estimated by the joint process estimator 60 using a noise reference signal n'(t) determined by the ratiometric method. Note that the scale of FIGS. 14 through 19 is not the same for each figure to better illustrate changes in each signal. FIGS. 18 and 19 illustrate the effect of the joint process estimator adaptive noise canceler using the noise reference signal n'(t), as determined by the reference processor of the present invention using the ratiometric method. Segments 18b and 19b are not dominated by motion induced noise as were segments 14b, 15b, and 16b of the measured signals. Additionally, segments 18a, 19a, 18c, and 19c have not been substantially changed from the measured signal segments 14a, 15a, 16a, 14c, 15c, and 16c where there was no motion induced noise.

Figure 20:
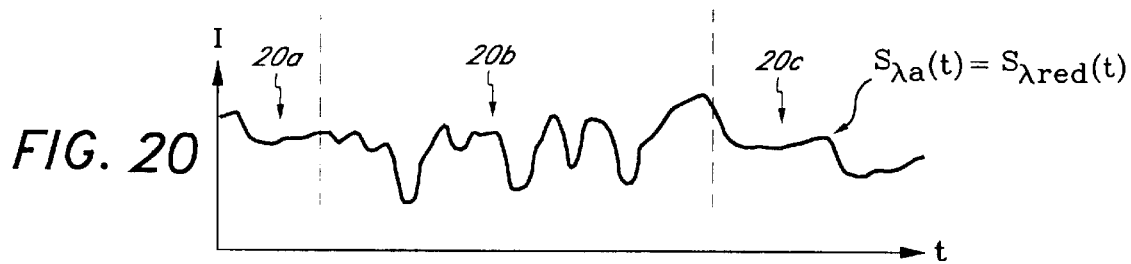
FIG. 20 illustrates a signal measured at a red wavelength $\lambda a=\lambda red=660$ nm for use in a processor of the present invention employing the constant saturation method for determining the noise reference signal n'(t) and for use in a joint process estimator. The measured signal comprises; a desired portion $Y_{\lambda a}(t)$ and an undesired portion $n_{\lambda a}(t)$.
Figure 21:
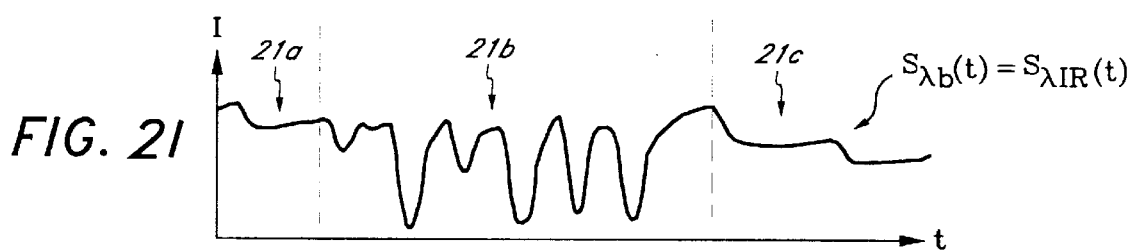
FIG. 21 illustrates a signal measured at an infrared wavelength $\lambda b=\lambda IR=940$ nm for use in a processor of the present invention employing the constant saturation method for determining the noise reference signal n'(t) and for use in a joint process estimator. The measured signal comprises a desired portion $Y_{\lambda b}(t)$ and an undesired portion $n_{\lambda b}(t)$.

Illustrating the operation of the constant saturation method of the present invention, FIGS. 20 and 21 show signals measured for input to a reference processor of the present invention which employs the constant saturation method, i.e., the signals $S_{\lambda a}(t) = S_{\lambda red}(t)$ and $S_{\lambda b}(t) = S_{\lambda IR}(t)$. A first segment 20a and 21a of each of the signals is relatively undisturbed by motion artifact, i.e., the patient did not move substantially during the time period in which these segments were measured. These segments 20a and 21a are thus generally representative of the desired plethysmographic waveform at each of the measured wavelengths. A second segment 20b and 21b of each of the signals is affected by motion artifact, i.e., the patient did move during the time period in which these segments were measured. Each of these segments 20b and 21b shows large motion induced excursions in the measured signal. A third segment 20c and 21c of each of the signals is again relatively unaffected by motion artifact and is thus generally representative of the desired plethysmographic waveform at each of the measured wavelengths.

Figure 22:
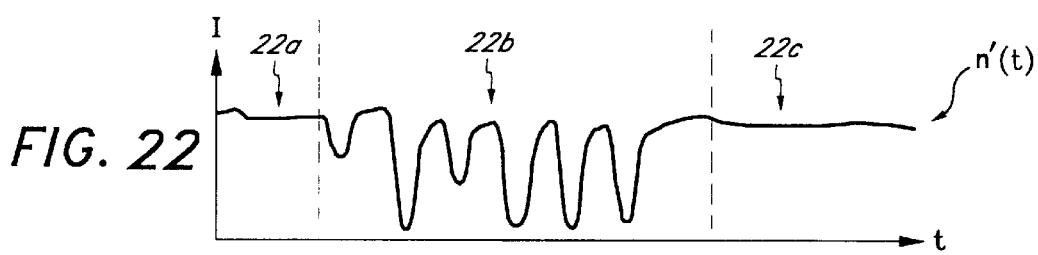
FIG. 22 illustrates the noise reference signal n'(t) determined by a processor of the present invention using the constant saturation method.

FIG. 22 shows the noise reference signal n'(t)=$n_{\lambda a}(t)$-$\omega_{a4} n_{\lambda b}(t)$, as determined by a reference processor of the present invention utilizing the constant saturation method. Again, the noise reference signal n'(t) is correlated to the undesired signal portions $n_{\lambda a}$ and $n_{\lambda b}$. Thus, a first segment 22a of the noise reference signal n'(t) is generally flat, corresponding to the fact that there is very little motion induced noise in the first segments 20a and 21a of each signal. A second segment 22b of the noise reference signal n'(t) exhibits large excursions, corresponding to the large motion induced excursions in each of the measured signals. A third segment 22c of the noise reference signal n'(t) is generally flat, again corresponding to the lack of motion artifact in the third segments 20b and 21c of each measured signal.

Figure 23:
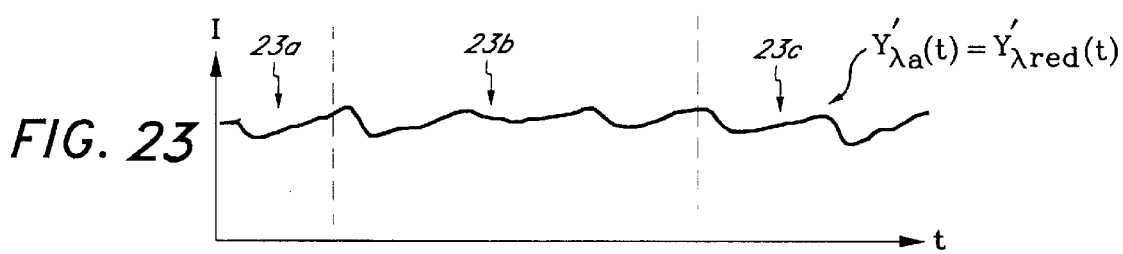
FIG. 23 illustrates a good approximation $Y'_{\lambda a}(t)$ to the desired portion $Y_{\lambda a}(t)$ of the signal $S_{\lambda a}(t)$ measured at $\lambda a=\lambda red=660$ nm estimated with a noise reference signal n'(t) determined by the constant saturation method.
Figure 24:
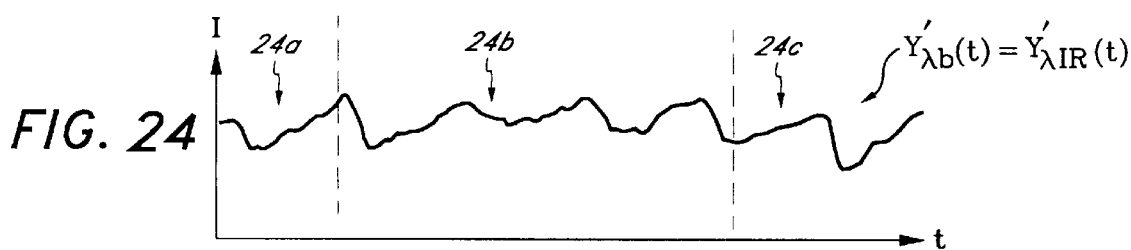
FIG. 24 illustrates a good approximation $Y'_{\lambda b}(t)$ to the desired portion $Y_{\lambda b}(t)$ of the signal $S_{\lambda b}(t)$ measured at $\lambda b=\lambda IR=940$ nm estimated with a noise reference signal n'(t) determined by the constant saturation method.

FIGS. 23 and 24 show the approximations $Y'_{\lambda a}(t)$ and $Y'_{\lambda b}(t)$ to the desired signals $Y_{\lambda a}(t)$ and $Y_{\lambda b}(t)$ as estimated by the joint process estimator 60 using a noise reference signal n'(t) determined by the constant saturation method. Note that the scale of FIGS. 20 through 24 is not the same for each figure to better illustrate changes in each signal. FIGS. 23 and 24 illustrate the effect of the joint process estimator adaptive noise canceler using the noise reference signal n'(t) as determined by a reference processor of the present invention utilizing the constant saturation method. Segments 23b and 24b are not dominated by motion induced noise as were segments 20b and 21b of the measured signals. Additionally, segments 23a, 24a, 23c, and 24c have not been substantially changed from the measured signal segments 20a, 21a, 20c, and 21c where there was no motion induced noise.

METHOD FOR ESTIMATING DESIRED PORTIONS OF MEASURED SIGNALS IN A PULSE OXIMETER

A copy of a computer program subroutine, written in the C programming language, calculates a noise reference signal n'(t) using the ratiometric method and, using a joint process estimator 60, estimates the desired signal portions of two measured signals, each having an undesired portion which is correlated to the noise reference signal n'(t) and one of which was not used to calculate the noise reference signal n'(t), is appended in Appendix A. For example, $S_{\lambda a}(t)=S_{\lambda red1}(t)=S_{\lambda 650nm}(t)$ and $S_{\lambda c}(t)=S_{\lambda IR}(t)=S_{\lambda 940nm}(t)$ can be input to the computer subroutine. One skilled in the art will realize that $S_{\lambda a}(t)=S_{\lambda red2}(t)=S_{\lambda 685nm}(t)$ and $S_{\lambda c}(t)=S_{\lambda IR}(t)=S_{\lambda 940nm}(t)$ will also work. This subroutine is one way to implement the steps illustrated in the flowchart of FIG. 8 for a monitor particularly adapted for pulse oximetry.

The program estimates the desired signal portions of two light energy signals, one preferably corresponding to light in the visible red range and the other preferably corresponding to light in the infrared range such that a determination of the amount of oxygen available to the body, or the saturation of oxygen in the arterial blood, may be made. The calculation of the saturation is performed in a separate subroutine. Various methods for calculation of the oxygen saturation are known to those skilled in the art. One such calculation is described in the articles by G. A. Mook, et al, and Michael R. Neuman cited above. Once the concentration of oxygenated hemoglobin and deoxygenated hemoglobin are determined, the value of the saturation is; determined similarly to equations (73) through (80) wherein measurements at times $t_1$ and $t_2$ are made at different, yet proximate times over which the saturation is relatively constant. For pulse oximetry, the average saturation at time $t=(t_1+t_2)/2$ is then determined by:

$$\text{Saturation}(t) = C_{HbO2}(t)/[C_{HbO2}(t)+C_{Hb}(t)]. \tag{95}$$

$$= \frac{\epsilon_{Hb,\lambda a} - \epsilon_{Hb,\lambda b}\left(\frac{\Delta Y_{\lambda a}}{\Delta Y_{\lambda b}}\right)}{\epsilon_{Hb,\lambda a} - \epsilon_{HbO2,\lambda a} - (\epsilon_{Hb,\lambda b} - \epsilon_{HbO2,\lambda b})\left(\frac{\Delta Y_{\lambda a}}{\Delta Y_{\lambda b}}\right)} \tag{96}$$

Using the ratiometric method, three signals $S_{\lambda a}(t)$, $S_{\lambda b}(t)$, and $S_{\lambda c}(t)$ are input to the subroutine. $S_{\lambda a}(t)$ and $S_{\lambda b}(t)$ are used to calculate the noise reference signal n'(t). As described above, the wavelengths of light at which $S_{\lambda a}(t)$ and $S_{\lambda b}(t)$ are measured are chosen to satisfy the relationship of equation (84). Once the noise reference signal n'(t) is determined, the desired signal portions $Y_{\lambda a}(t)$ and $Y_{\lambda c}(t)$ of the measured signals $S_{\lambda a}(t)$ and $S_{\lambda c}(t)$ are estimated for use in calculation of the oxygen saturation.

The correspondence of the program variables to the variables defined in the discussion of the joint process estimator is as follows:
$\Delta_m(t)$=nc[ ].Delta
$\Gamma_{f,m(t)}$=nc[ ].fref
$\Gamma_{b,m}(t)$=nc[ ].bref
$f_m(t)$=nc[ ].ferr
$b_m(t)$=nc[ ].berr
$\Im_m(t)$=nc[ ].Fswsqr
$\beta_m(t)$=nc[ ].Bswsqr
$\gamma_m(t)$=nc[ ].Gamma
$\rho_{m,\lambda a}(t)$=nc[ ].Roh_a
$\rho_{m,\lambda c}(t)$=nc[ ].Roh_c
$\epsilon_{m,\lambda a}(t)$=nc[ ].err_a
$\epsilon_{m,\lambda c}(t)$=nc[ ].err_c
$\kappa_{m,\lambda a}(t)$=nc[ ].K_a
$\kappa_{m,\lambda c}(t)$=nc[ ].K_c A first portion of the program performs the initialization of the registers 90, 92, 96, and 98 and intermediate variable values as in the "INITIALIZE NOISE CANCELER" box 120 and equations (40) through (44) and equations (61), (62), (65), and (66). A second portion of the program performs the time updates of the delay element variables 110 where the value at the input of each delay element-variable 110 is stored in the delay element variable 110 as in the "TIME UPDATE OF [$Z^{-1}$] ELEMENTS" box 130.

A third portion of the program calculates the noise reference signal, as in the "CALCULATE NOISE REFERENCE (n'(t)) FOR TWO MEASURED SIGNAL SAMPLES" box 140 using the proportionality constant $\omega_{r4}$ determined by the ratiometric method as in equation (85).

A fourth portion of the program performs the zero-stage update as in the "ZERO-STAGE UPDATE" box 150 where the zero-stage forward prediction error $f_0(t)$ and the zero-stage backward prediction error $b_0(t)$ are set equal to the value of the noise reference signal n'(t) just calculated. Additionally, zero-stage values of intermediate variables $\Im_0(t)$ and $\beta_0(t)$ (nc[ ].Fswsqr and nc[ ].Bswsqr in the program) are calculated for use in setting register 90, 92, 96, and 98 values in the least-squares lattice predictor 70 and the regression filters 80a and 80b.

A fifth portion of the program is an iterative loop wherein the loop counter, m, is reset to zero with a maximum of m=NC_CELLS, as in the "m=0" box 160 in FIG. 8. NC_CELLS is a predetermined maximum value of iterations for the loop. A typical value of NC_CELLS is between 60 and 80, for example. The conditions of the loop are set such that the loop iterates a minimum of five times and continues to iterate until a test for conversion is met or m=NC_CELLS. The test for conversion is whether or not the sum of the weighted sun of forward prediction errors plus the weighted sum of backward prediction errors is less than a small number, typically 0.00001 (i.e, $\Im_m(t)+\beta_m(t)$ $\leq 0.00001$).

A sixth portion of the program calculates the forward and backward reflection coefficient $\Gamma_{m,f}(t)$ and $\Gamma_{m,b}(t)$ register 90 and 92 values (nc[ ].fref and nc[ ].bref in the program) as in the "ORDER UPDATE $m^{th}$-STAGE OF LSL-PREDICTOR" box 170 and equations (49) and (50). Then forward and backward prediction errors $f_m(t)$ and $b_m(t)$ (nc[ ].ferr and nc[ ].berr in the program) are calculated as in equations (51) and (52). Additionally, intermediate variables $\Im_m(t)$, $\beta_m(t)$ and $\gamma_m(t)$ (nc[ ].Fswsqr, nc[ ].Bswsqr, nc[ ].Gamma in the program) are calculated, as in equations (53), (54), and (55). The first cycle of the loop uses the values for nc[0].Fswsqr and. nc[0].Bswsqr calculated in the ZERO-STAGE UPDATE portion of the program.

A seventh portion of the program, still within the loop, calculates the regression coefficient $\kappa_{m,\lambda a}(t)$ and $\kappa_{m,\lambda c}(t)$ register 96 and 98 values (nc[ ].K_a and nc[ ].K_c in the program) in both regression filters, as in the "ORDER UPDATE $m^{th}$ STAGE OF REGRESSION FILTER(S)" box 180 and equations (57) through (68). Intermediate error signals and variables $\epsilon_{m,\lambda a}(t)$, $\epsilon_{m,\lambda c}(t)$, and $\rho_{m,\lambda a}(t)$ $\rho_{m,\lambda c}(t)$ (nc[ ].err_a and nc[ ].err_c, nc[ ].roh_a, and nc[ ].roh_c in the subroutine) are also calculated as in equations (58), (64), (56), and (60), respectively.

The test for convergence of the joint process estimator is performed each time the loop iterates, analogously to the "DONE" box 190. If the sum of the weighted sums of the forward and backward prediction errors $\Im_m(t)+\beta_m(t)$ is less than or equal to 0.00001, the loop terminates. Otherwise, the sixth and seventh portions of the program repeat.

When either the convergence test is passed or m=NC_CELLS, an eighth portion of the program calculates the output of the joint process estimator 60 adaptive noise canceler as in the "CALCULATE OUTPUT" box 200. This output is a good approximation to both of the desired signals $Y'_{\lambda a}(t)$ and $Y'_{\lambda c}(t)$ for the set of samples $S_{\lambda a}(t)$, $S_{\lambda b}(t)$, and $S_{\lambda c}(t)$ input to the program. After many sets of samples are processed by the joint process estimator, a compilation of the outputs provides output waves which are good approximations to the plethysmographic wave at each wavelength, $\lambda a$ and $\lambda c$.

Another copy of a computer program subroutine, written in the C programming language, which calculates a noise reference signal n'(t) using the constant saturation method and, using a joint process estimator 60, estimates a good approximation to the desired signal portions of two measured signals, each having an undesired portion which is correlated to the noise reference signal n'(t) and each having been used to calculate the noise reference signal n'(t), is appended in Appendix B. This subroutine is another way to implement the steps illustrated in the flowchart of FIG. 8 for a monitor particularly adapted for pulse oximetry. The two signals are measured at two different wavelengths $\lambda a$ and $\lambda b$, where $\lambda a$ is typically in the visible region and $\lambda b$ is typically in the infrared region. For example, in one embodiment of the present invention, tailored specifically to perform pulse oximetry using the constant saturation method, $\lambda a=660$ nm and $\lambda b=940$ nm.

The correspondence of the program variables to the variables defined in the discussion of the joint process estimator is as follows:

$\Delta_m(t)$=nc[ ]. Delta
$\Gamma_{f,m(t)}$=nc[ ].fref
$\Gamma_{b,m}(t)$=nc[ ].bref
$f_m(t)$=nc[ ].ferr
$b_m(t)$=nc[ ].berr
$\Im_m(t)$=nc[ ].Fswsqr
$\beta_m(t)$=nc[ ].Bswsqr
$\gamma(t)$=nc[ ].Gamma
$\rho_{m,\lambda a}(t)$=nc[ ].Roh_a
$\rho_{m,\lambda b}(t)$=nc[ ].Roh_b
$\epsilon_{m,\lambda a}(t)$=nc[ ].err_a
$\epsilon_{m,\lambda b}(t)$=nc[ ].err_b
$\kappa_{m,\lambda a}(t)$=nc[ ].K_a
$\kappa_{m,\lambda b}(t)$=nc[ ].K_b First and second portions of the subroutine are the same as the first and second portions of the above described subroutine tailored for the ratiometric method of determining the noise reference signal n'(t).

A third portion of the subroutine calculates the noise reference signal, as in the "CALCULATE NOISE REFERENCE (n'(t)) FOR TWO MEASURED SIGNAL SAMPLES" box 140 for the signals $S_{\lambda a}(t)$ and $S_{\lambda b}(t)$ using the a proportionality constant $\omega_{a4}(t)$ determined by the constant saturation method as in equations (90) and (91). The saturation is calculated in a separate subroutine and a value of $\omega_{a4}(t)$ is imported to the present subroutine for estimating the desired portions $Y_{\lambda a}(t)$ and $Y_{\lambda a}(t)$ of the composite measured signals $S_{\lambda a}(t)$ and $S_{\lambda b}(t)$.

Fourth, fifth, and sixth portions of the subroutine are similar to the fourth, fifth, and sixth portions of the above described program tailored for the ratiometric method. However, the signals being used to estimate the desired signal portions $Y_{\lambda a}(t)$ and $Y_{\lambda b}(t)$ in the present subroutine tailored for the constant saturation method, are $S_{\lambda a}(t)$ and $S_{\lambda b}(t)$, the same signals that were used to calculate the noise reference signal n'(t).

A seventh portion of the program, still within the loop begun in the fifth portion of the program, calculates the regression coefficient register 96 and 98 values $\kappa_{m,\lambda a}(t)$ and $\kappa_{m,\lambda b}(t)$ (nc[ ].K_a and nc[ ].K_b in the program) in both regression filters, as in the "ORDER UPDATE $m^{th}$ STAGE OF REGRESSION FILTER(S)" box 180 and equations (57) through (67). Intermediate error signals and variables $\epsilon_{m,\lambda a}(t)$, $\epsilon_{m,\lambda b}(t)$, $\rho_{m,\lambda a}(t)$ and $\rho_{m,\lambda b}(t)$ (nc[ ].err_a and nc[ ].err_b, nc[ ].roh_a, and nc[ ].roh_b in the subroutine) are also calculated as in equations (58), (63), (56), and (59), respectively.

The loop iterates until the test for convergence is passed, the test being the same as described above for the subroutine tailored for the ratiometric method. The output of the present subroutine is a good approximation to the desired signals $Y'_{\lambda a}(t)$ and $Y'_{\lambda b}(t)$ for the set of samples $S_{\lambda a}(t)$ and $S_{\lambda b}(t)$ input to the program. After approximations to the desired signal portions of many sets of measured signal samples are estimated by the joint process estimator, a compilation of the outputs provides waves which are good approximations to the plethysmographic wave at each wavelength, $\lambda a$ and $\lambda b$. The estimating process of the iterative loop is the same in either subroutine, only the sample values $S_{\lambda a}(t)$ and $S_{\lambda c}(t)$ or $S_{\lambda a}(t)$ and $S_{\lambda b}(t)$ input to the subroutine for use in estimation of the desired signal portions $Y_{\lambda a}(t)$ and $Y_{\lambda c}(t)$ or $Y_{\lambda a}(t)$ and $Y_{\lambda b}(t)$ and how the noise reference signal n'(t) is calculated are different for the ratiometric method and the constant saturation methods.

Independent of the method used, ratiometric or constant saturation, the approximations to the desired signal values $Y'_{\lambda a}(t)$ and $Y'_{\lambda c}(t)$ or $Y'_{\lambda a}(t)$ and $Y'_{\lambda b}(t)$ are input to a separate subroutine in which the saturation of oxygen in the arterial blood is calculated. If the constant saturation method is used, the saturation calculation subroutine also determines a value for the proportionality constant $\omega_{a4}(t)$ as defined in equations (90) and (91) and discussed above. The concentration of oxygenated arterial blood can be found from the approximations to the desired signal values since the desired signals are made up of terms comprising x(t), the thickness of arterial blood in¯ the finger; absorption coefficients of oxygenated and de-oxygenated hemoglobin, at each measured wavelength; and $C_{HbO2}(t)$ and $C_{Hb}(t)$, the concentrations of oxygenated and de-oxygenated hemoglobin, respectively. The saturation is a ratio of the concentration of one constituent, $A_5$, with respect to the total concentration of constituents in the volume containing $A_5$ and $A_6$. Thus, the thickness, x(t), is divided out of the saturation calculation and need not be predetermined. Additionally, the absorption coefficients are constant all each wavelength. The saturation of oxygenated arterial blood is then determined as in equations (95) and (96).

While one embodiment of a physiological monitor incorporating a processor of the present invention for determining a noise reference signal for use in an adaptive noise canceler to remove erratic noise components from a physiological measurement has been described in the form of a pulse oximeter, it will be obvious to one skilled in the art that other types of physiological monitors may also employ the above described techniques for noise reduction on a composite measured signal in the presence of noise.

Furthermore, it will be understood that transformations of measured signals other than logarithmic conversion and determination of a proportionality factor which allows removal of the desired signal portions for determination of a noise reference signal are possible. Additionally, although the proportionality factor $\omega$ has been described herein as a ratio of a portion of a first signal to a portion of a second signal, a similar proportionality constant determined as a ratio of a portion of a second signal to a portion of a first signal could equally well be utilized in the processor of the present invention. In the latter case, a noise reference signal would generally resemble $n'(t)=n_{\lambda b}(t)-\omega n_{\lambda a}(t)$.

It will also be obvious to one skilled in the art that for most physiological measurements, two wavelengths may be determined which will enable a signal to be measured which is indicative of a quantity of a component about which information is desired. Information about a constituent of any energy absorbing physiological material may be determined by a physiological monitor incorporating a signal processor of the present invention and an adaptive noise canceler by determining wavelengths which are absorbed primarily by the constituent of interest. For most physiological measurements, this is a simple determination.

Moreover, one skilled in the art will realize that any portion of a patient or a material derived from a patient may be used to take measurements for a physiological monitor incorporating a processor of the present invention and an adaptive noise canceler. Such areas include a digit such as a finger, but are not limited to a finger.

One skilled in the art will realize that many different types of physiological monitors may employ a signal processor of the present invention in conjunction with an adaptive noise canceler. Other types of physiological monitors include, but are in not limited to, electron cardiographs, blood pressure monitors, blood gas saturation (other than oxygen saturation) monitors, capnographs, heart rate monitors, respiration monitors, or depth of anesthesia monitors. Additionally, monitors which measure the pressure and quantity of a substance within the body such as a breathalizer, a drug monitor, a cholesterol monitor, a glucose monitor, a carbon dioxide monitor, a glucose monitor, or a carbon monoxide monitor may also employ the above described techniques for removal of undesired signal portions.

Furthermore, one skilled in the art will realize that the above described techniques of noise removal from a composite signal including noise components can also be performed on signals made up of reflected energy, rather than transmitted energy. One skilled in the art will also realize that a desired portion of a measured signal of any type of energy, including but not limited to sound energy, X-ray energy, gamma ray energy, or light energy can be estimated by the noise removal techniques described above. Thus, one skilled in the art will realize that the processor of the present invention and an adaptive noise canceler can be applied in such monitors as those using ultrasound where a signal is transmitted through a portion of the body and reflected back from within the body back through this portion of the body. Additionally, monitors such as echo cardiographs may also utilize the techniques of the present invention since they too rely on transmission and reflection.

While the present invention has been described in terms of a physiological monitor, one skilled in the art will realize that the signal processing techniques of the present invention can be applied in many areas, including but not limited to the processing of a physiological signal. The present invention may be applied in any situation where a signal processor comprising a detector receives a first signal which includes a first desired signal portion and a first undesired signal portion and a second signal which includes a second desired signal portion and a second undesired signal portion. The first and second signals propagate through a common medium and the first and second desired signal portions are correlated with one another. Additionally, at least a portion of the first and second undesired signal portions are correlated with one another due to a perturbation of the medium while the first and second signals are propagating through the, medium. The processor receives the first and second signals and combines the first and second signals to generate a noise reference signal in which the primary component is derived from the first and second undesired signal portions. Thus, the signal processor of the present invention is readily applicable to numerous signal processing areas.

```
/*****************************************************************
************************* APPENDIX A ****************************
************************* Least square Lattice ******************
********************* Noise Cancelling **************************
/* Example for ratiometric approach to noise cancelling */
#define LAMBDA 0.95
void OxiLSL_NC (int     reset,
                int     passes,
                int     *signal_1,
                int     *signal_2,
                int     *signal_3,
                int     *target_1,
                int     *target_2) {
    int     i, ii, k, m, n, contraction;
    static int      *s_a, *s_b, *s_c, *out_a, *out_c;
    static float    Delta_sqr, scale, noise_ref;
    if(reset == TRUE) {
        s_a = signal_1;
        s_b = signal_2;
        s_c = signal_3;
        out_a = target_1;
        out_c = target_2;
        factor = 1.5;
        scale = 1.0/4160.0;
        /* noise canceller initialization at time t = 0 */
        nc[0].berr = 0.0;
        nc[0].Gamma = 1.0;
        for(m = 0; m<NC_CELLS; m++) {
            nc[m].err_a = 0.0;
            nc[m].err_b = 0.0;
            nc[m].Roh_a = 0.0;
            nc[m].Roh_c = 0.0;
            nc[m].Delta = 0.0;
```

-continued

```
        nc[m].Fswsqr = 0.00001;
        nc[m].Bswsqr = 0.00001;
      }
    }
/*========================= END INITIALIZATION ==========================*/
    for(k= 0; k<passes; k++) {
      contraction = FALSE;
      for (m=0; m<NC_CELLS; m++) {        /* Update delay elements */
        nc[m].berr1 = nc[m].berr;
        nc[m].Bswsqr1 = nc[m].Bswsqr;
      }
      noise_ref = factor * log(1.0 - (*s_a) * scale)
                       - log(1.0 - (*s_b) * scale) ;
      nc[0].err_a = log(1.0 - (*s_b) * scale);
      nc[0 .err_b = log(1.0 - (*s_c) * scale);
      ++s_a;
      ++s_b;
      ++s_c;
      nc[0].ferr = noise_ref;
      nc[0].berr = noise_ref;
      nc[0].Fswsqr = LAMBDA * nc[0].Fswsqr + noise_ref * noise_ref;
      nc[0].Bswsqr = nc[0].Fswsqr;
      /* Order Update */
      for(n=1;(n < NC_CELLS) && (contraction == FALSE); n++) {
        /* Adaptive Lattice Section */
        m = n-1;
        ii = n-1;
        nc[m].Delta *= LAMBDA;
        nc[m].Delta += nc[m].berr1 * nc[m].ferr / nc[m].Gamma;
        Delta_sqr = nc[m].Delta * nc[m].Delta;
        nc[n].fref = -nc[m].Delta / nc[m].Bswsqr1;
        nc[n].bref = -nc[m].Delta / nc[m].Fswsqr;
        nc[n].ferr = nc[m].ferr + nc[n].fref * nc[m].berr1;
        nc[n].berr = nc[m].berr1 + nc[n].bref * nc[m].ferr;
        nc[n].Fswsqr = nc[m].Fswsqr - Delta_sqr / nc[m].Bswsqr1;
        nc[n].Bswsqr1 = nc[m].Bswsqr1 - Delta_sqr / nc[m].Fswsqr;
        if( (nc[n].Fswsqr + nc[n].Bswsqr) > 0.00001 || (n < 5) ) {
          nc[n].Gamma = nc[m].Gamma - nc[m].berr1 * nc[m].berr1 / nc[m].Bswsqr1;
          if(nc[n].Gamma < 0.05) nc[n].Gamma = 0.05;
          if(nc[n].Gamma > 1.00) nc[n].Gamma = 1.00;
        /* Joint Process Estimation Section */
          nc[m].Roh_a *= LAMBDA;
          nc[m].Roh_a += nc[m].berr * nc[m].err_a / nc[m].Gamma ;
          nc[m].k_a = nc[m].Roh_a / nc[m].Bswsqr;
          nc[n].err_a = nc[m].err_a - nc[m].k_a * nc[m].berr;
          nc[m].Roh_c *= LAMBDA;
          nc[m].Roh_c += nc[m].berr * nc[m].err_b / nc[m].Gamma ;
          nc[m].k_c = nc[m].Roh_c / nc[m].Bswsqr;
          nc[n].err_b = nc[m].err_b - nc[m].k_c * nc[m].berr;
        }
        else {
          contraction = TRUE;
          for(i=n; i<NC_CELLS; i++) {
            nc[i].err_a = 0.0;
            nc[i].Roh_a = 0.0;
            nc[i].err_b = 0.0;
            nc[i].Roh_c = 0.0;
            nc[i].Delta = 0.0;
            nc[i].Fswsqr = 0.00001;
            nc[i].Bswsqr = 0.00001;
            nc[i].Bswsqr1 = 0.00001;
          }
        }
      }
      *out_a++ = (int) ( (-exp(nc[ii].err_a) +1.0) / scale) ;
      *out_c++ = (int) ( (-exp(nc[ii].err_b) +1.0) / scale) ;
    }
  }
}
/********************** Least Square Lattice **************************
**********************                       **************************
***********************************************************************
***********************************************************************
************************ APPENDIX A ***********************************
************************ Least square Lattice *************************
************************ Noise Cancelling *****************************
/* Example for constant saturation approach to noise cancelling */
#define LAMBDA 0.95
void OxiLSL_NC( int     reset,
                int     passes,
```

```
                    int     sat_factor,
                    int     *signal_1,
                    int     *signal_2,
                    int     *target_1,
                    int     *target_2) {
    int     i, ii, k, m, n, contraction;
static int      *s_a, *s_b, *out_a, *out_b;
static float    Delta_sqr, scale, noise_ref;
    if(reset == TRUE) {
        s_a = signal_1;
        s_b = signal_2;
        out_a = target_1;
        out_b = target_2;
        scale = 1.0/4160.0;
        /* noise canceller initialization at time t = 0 */
        nc[0].berr = 0.0;
        nc[0].Gamma = 1.0;
        for(m = 0; m<NC_CELLS; m++) {
            nc[m].err_a = 0.0;
            nc[m].err_b = 0.0;
            nc[m].Roh_a = 0.0;
            nc[m].Roh_b = 0.0;
            nc[m].Delta = 0.0;
            nc[m].Fswsqr = 0.00001;
            nc[m].Bswsqr = 0.00001;
        }
    }
/*========================= END INITIALIZATION =========================*/
    for(k= 0; k<passes; k++) {
        contraction = FALSE;
        for (m=0; m<NC_CELLS; m++) {         /* Update delay elements */
            nc[m].berr1 = nc[m].berr;
            nc[m].Bswsqr1 = nc[m].Bswsqr;
        }
        noise_ref = factor * log(1.0 - (*s_a) * scale)
                           - log(1.0 - (*s_b) * scale) ;
        nc[0].err_a = log(1.0 - (*s_a) * scale);
        nc[0 .err_b = log(1.0 - (*s_b) * scale);
        ++s_a;
        ++s_b;
        nc[0].ferr = noise_ref;
        nc[0].berr = noise_ref;
        nc[0].Fswsqr = LAMBDA * nc[0].Fswsqr + noise_ref * noise_ref;
        nc[0].Bswsqr = nc[0].Fswsqr;
        /* Order Update */
        for(n=1;(n < NC_CELLS) && (contraction == FALSE); n++) {
            /* Adaptive Lattice Section */
            m = n-1;
            ii = n-1;
            nc[m].Delta *= LAMBDA;
            nc[m].Delta += nc[m].berr1 * nc[m].ferr / nc[m].Gamma;
            Delta_sqr = nc[m].Delta * nc[m].Delta;
            nc[n].fref = -nc[m].Delta / nc[m].Bswsqr1;
            nc[n].bref = -nc[m].Delta / nc[m].Pswsqr;
            nc[n].ferr = nc[m].ferr + nc[n].fref * nc[m].berr1;
            nc[n].berr = nc[m].berr1 + nc[n].bref * nc[m].ferr;
            nc[n].Fswsqr = nc[m].Fswsqr - Delta_sqr / nc[m].Bswsqr1;
            nc[n].Bswsqr = nc[m].Bswsqr1 - Delta_sqr / nc[m].Fswsqr;
            if( (nc[n].Fswsqr + nc[n].Bswsqr) > 0.00001 || (n < 5) ) {
                nc[n].Gamma = nc[m].Gamma - nc[m].berr1 * nc[m].berr1 / nc[m].Bswsqr1;
                if(nc[n].Gamma < 0.05) nc[n].Gamma = 0.05;
                if(nc[n].Gamma > 1.00) nc[n].Gamma = 1.00;
                /* Joint Process Estimation Section */
                nc[m].Roh_a *= LAMBDA;
                nc[m].Roh_a += nc[m].berr * nc[m].err_a / nc[m].Gamma ;
                nc[m].k_a = nc[m].Roh_a / nc[m].Bswsqr;
                nc[n].err_a = nc[m].err_a - nc[m].k_a * nc[m].berr;
                nc[m].Roh_b *= LAMBDA;
                nc[m].Roh_b += nc[m].berr * nc[m].err_b / nc[m].Gamma ;
                nc[m].k_b = nc[m].Roh_b / nc[m].Bswsqr;
                nc[n].err_b = nc[m].err_b - nc[m].k_b * nc[m].berr;
            }
            else {
                contraction = TRUE;
                for(i=n; i<NC_CELLS; i++) {
                    nc[i].err_a = 0.0;
                    nc[i].Roh_a = 0.0;
                    nc[i].err_b = 0.0;
                    nc[i].Roh_b = 0.0;
```

-continued

```
        nc[i].Delta = 0.0;
        nc[i].Fswsqr = 0.00001;
        nc[i].Bswsqr = 0.00001;
        nc[i].Bswsqr1 = 0.00001;
      }
    }
  }
  *out_a++ = (int) ( (-exp(nc[ii].err_a) +1.0) / scale) ;
  *out_b++ = (int) ( (-exp(nc[ii].err_b) +1.0) / scale) ;
  }
}
/******************** Least Square Lattice **************************
*********************                      ***************************
**********************************************************************
```

What is claimed:

1. A physiological monitoring apparatus comprising:

means for acquiring a first signal comprising a first desired signal portion and a first undesired signal portion and a second signal comprising a second desired signal portion and a second undesired signal portion;

an adaptive canceler having a reference input for receiving a reference signal and a signal input for receiving said first and said second signals, wherein said adaptive canceler generates an output signal which approximates said first desired signal portion and said second desired portion; and a processor responsive to the output of said adaptive canceler to calculate a physiological parameter.

2. The physiological monitoring apparatus as defined in claim 1 wherein said adaptive noise canceler further comprises a joint process estimator.

3. The physiological monitoring apparatus as defined in claim 2 wherein said joint process estimator further comprises a least-squares lattice predictor in conjunction with a regression filter.

4. A pulse oximeter comprising:

at least first and second light emitting devices;

at least one light detector configured to receive light attenuated by transmission through a living tissue with arterial pulsing blood, the light detector acquiring a first signal based on the first light emitting device comprising a first desired signal portion and a first undesired signal portion and a second signal based on the second light emitting device comprising a second desired signal portion and a second undesired signal portion;

an adaptive filter which filters the first and the second signals through use of an estimate of the first or the second undesired signal portion, wherein the adaptive filter generates an output signal which approximates the first desired signal portion and the second desired signal portion; and a processor responsive to the output of the adaptive filter to calculate oxygen saturation.

5. The pulse oximeter of claim 4, wherein the adaptive filter uses a least squares algorithm.

6. The pulse oximeter of claim 5, wherein the adaptive filter is an adaptive noise canceler.

7. The pulse oximeter of claim 6, wherein the adaptive filter uses a least squares lattice.

8. The pulse oximeter of claim 7, further comprising a display to display the oxygen saturation.

9. A pulse oximeter comprising:

at least first and second light emitting devices;

at least one light detector configured to receive light attenuated by transmission through a living tissue with arterial blood, the light detector generating a first signal based on the first light emitting device and a second signal based on the second light emitting device;

a filter responsive to signals representing the first and second signals to filter the first and the second signals, wherein the filter adjusts its transfer function in response to changes in at least one of the first and the second signals and in response to an evaluation of an error to optimize at least one of a first and a second filtered output signals; and a processor calculator responsive to the first and the second filtered output signals to calculate oxygen saturation.

10. The pulse oximeter of claim 9, wherein the filter uses a least squares algorithm to adjust its transfer function.

11. The pulse oximeter of claim 10, wherein the filter is an adaptive noise canceler.

12. The pulse oximeter of claim 11, wherein the filter is a least squares lattice.

13. The pulse oximeter of claim 9, wherein the filter uses a least means squares algorithm.

14. The pulse oximeter of claim 9, further comprising a display to display the oxygen saturation.

15. A method of calculating blood oxygen saturation comprising the steps of:

transmitting light of at least first and second wavelengths through body tissue carrying blood to a light-sensitive detector to generate first and second measured intensity signals;

adaptively filtering representations of the first and second measured intensity signals to provide first and second filtered signals; and calculating oxygen saturation based upon the first and second filtered signals.

16. The method of claim 15, wherein the adaptive filtering uses a least squares algorithm.

17. The method of claim 15, wherein the adaptive filtering uses a least squares lattice.

18. The method of claim 15, wherein the adaptive filtering uses an adaptive noise canceler.

19. The method of claim 15 further comprising displaying the oxygen saturation.

20. A method of calculating blood oxygen saturation comprising the steps of:

transmitting light of at least first and second wavelengths through body tissue carrying blood to a light-sensitive detector to generate first and second signals;

filtering the first and the second signals, wherein the filtering comprises adjusting a filter transfer function in response to changes in at least one of the first and the second signals and in response to an evaluation of an error, and wherein the filtering optimizes at least one of a first and a second filtered output signal; and calculating oxygen saturation based upon the first and the second filtered output signals.

21. The method of claim 20, wherein the filtering uses a least squares algorithm to adjust the transfer function.

22. The method of claim 20, wherein the filtering uses a least means squares algorithm to adjust the transfer function.

23. The method of claim 20, wherein the filter is a least squares lattice.

24. The method of claim 20, wherein the filter is an adaptive noise canceler.

25. The method of claim 20, further comprising displaying the oxygen saturation.

26. A pulse oximeter comprising:

a light emitter adapted to emit light of at least first and second wavelengths;

at least one light detector configured to receive light attenuated by transmission through a living tissue with arterial pulsing blood, the light detector acquiring a first signal based on the first wavelength and a second signal based on the second wavelength;

an analog to digital converter that digitizes the first and the second signals to produce digitized first and second signals;

an adaptive signal processor responsive to the first and the second digitized signals to filter the first and the second digitized signals, to produce adaptively filtered first and second signals; and a processor responsive to the adaptively filtered first and second signals to calculate oxygen saturation.

27. The pulse oximeter of claim 26, wherein the adaptive signal processor uses a least squares algorithm.

28. The pulse oximeter of claim 26, wherein the adaptive signal processor is configured as a least squares lattice.

29. The pulse oximeter of claim 26, wherein the adaptive signal processor is configured as an adaptive noise canceler.

30. The pulse oximeter of claim 26, further comprising a display to display the oxygen saturation.

\* \* \* \* \*